United States Patent
Ross et al.

(10) Patent No.: US 11,186,791 B2
(45) Date of Patent: Nov. 30, 2021

(54) COMPOSITION, METHOD AND USE

(71) Applicant: Innospec Limited, Ellesmere Port (GB)

(72) Inventors: Alan Norman Ross, Wigan (GB); Martin Roberts, Preston (GB)

(73) Assignee: Innospec Limited, Ellesmere Port (GB)

( * ) Notice: Subject to any disclaimer, the term of this patent is extended or adjusted under 35 U.S.C. 154(b) by 0 days.

(21) Appl. No.: 16/496,162

(22) PCT Filed: Mar. 28, 2018

(86) PCT No.: PCT/GB2018/050846
§ 371 (c)(1),
(2) Date: Sep. 20, 2019

(87) PCT Pub. No.: WO2018/178692
PCT Pub. Date: Oct. 4, 2018

(65) Prior Publication Data
US 2020/0157445 A1 May 21, 2020

(30) Foreign Application Priority Data
Mar. 30, 2017 (GB) ..................... 1705089

(51) Int. Cl.
| | |
|---|---|
| *C10L 1/222* | (2006.01) |
| *C10L 1/19* | (2006.01) |
| *C10L 10/18* | (2006.01) |
| *C10L 1/223* | (2006.01) |
| *C07C 211/63* | (2006.01) |
| *C07C 215/40* | (2006.01) |
| *C07C 217/08* | (2006.01) |
| *C10L 10/08* | (2006.01) |
| *C07C 209/24* | (2006.01) |
| *C07C 213/04* | (2006.01) |
| *C07C 69/40* | (2006.01) |
| *C07C 67/317* | (2006.01) |
| *C10M 133/06* | (2006.01) |

(52) U.S. Cl.
CPC .......... *C10L 1/2222* (2013.01); *C07C 67/317* (2013.01); *C07C 69/40* (2013.01); *C07C 209/24* (2013.01); *C07C 211/63* (2013.01); *C07C 213/04* (2013.01); *C07C 215/40* (2013.01); *C07C 217/08* (2013.01); *C10L 1/1905* (2013.01); *C10L 1/2235* (2013.01); *C10L 10/08* (2013.01); *C10L 10/18* (2013.01); *C10M 133/06* (2013.01); *C10L 2200/0259* (2013.01); *C10L 2200/0423* (2013.01); *C10L 2230/22* (2013.01); *C10L 2270/023* (2013.01); *C10M 2207/288* (2013.01); *C10M 2215/04* (2013.01)

(58) Field of Classification Search
CPC ... C07C 201/00; C07C 209/24; C07C 211/63; C07C 213/04; C07C 215/40; C07C 217/08; C07C 217/48; C07C 67/317; C07C 69/34; C07C 69/40; C10L 10/08; C10L 10/18; C10L 1/1905; C10L 1/2222; C10L 1/2235; C10L 2200/0259; C10L 2200/0423; C10L 2230/22; C10L 2270/02; C10L 2270/023; C10M 133/06; C10M 2207/288; C10M 2215/02; C10M 2215/04; C10M 2215/042; C10N 2030/04
See application file for complete search history.

(56) References Cited

U.S. PATENT DOCUMENTS

| | | |
|---|---|---|
| 2,812,342 A | 11/1957 | Peters |
| 3,110,673 A | 11/1963 | Benoit, Jr. |
| 3,172,892 A | 3/1965 | Le Suer |
| 3,216,936 A | 11/1965 | Le Suer |
| 3,219,666 A | 11/1965 | Norman |
| 3,250,715 A | 5/1966 | Wyman |
| 3,251,853 A | 5/1966 | Hoke |
| 3,260,671 A | 7/1966 | Trites |
| 3,272,746 A | 9/1966 | Le Suer |
| 3,275,554 A | 9/1966 | Wagenaar |

(Continued)

FOREIGN PATENT DOCUMENTS

| | | |
|---|---|---|
| EP | 2811007 A1 | 7/2013 |
| EP | 2796446 A | 4/2014 |

(Continued)

OTHER PUBLICATIONS

International Search Report and Written Opinion issued in PCT/GB2018/050846 dated May 28, 2018.

(Continued)

*Primary Examiner* — Ellen M Mcavoy
*Assistant Examiner* — Chantel L Graham
(74) *Attorney, Agent, or Firm* — Burns & Levinson LLP; Janine M. Susan

(57) ABSTRACT

A quaternary ammonium compound of formula (I): (I) wherein $R^0$, $R^1$, $R^2$ and $R^3$ is each independently an optionally substituted hydrocarbyl group, X is a linking group, $R^4$ is an optionally substituted alkylene group, R5 is hydrogen or an optionally substituted alkyl, alkenyl or aryl group, and n is 0 or a positive integer, provided that n is not 0 when R5 is hydrogen.

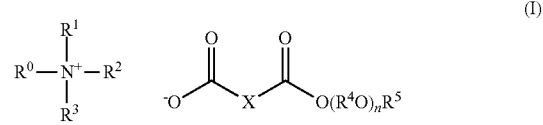

30 Claims, No Drawings

(56) References Cited

U.S. PATENT DOCUMENTS

| | | | |
|---|---|---|---|
| 3,310,492 A | 3/1967 | Benoit, Jr. |
| 3,326,801 A | 6/1967 | Schloholam |
| 3,337,459 A | 8/1967 | Ford |
| 3,341,542 A | 9/1967 | Le Suer |
| 3,405,064 A | 10/1968 | Miller |
| 3,429,674 A | 2/1969 | Hoke |
| 3,438,757 A | 4/1969 | Honnen |
| 3,444,170 A | 5/1969 | Norman |
| 3,454,555 A | 7/1969 | van der Voort |
| 3,455,831 A | 7/1969 | Davis |
| 3,455,832 A | 7/1969 | Davis |
| 3,468,639 A | 9/1969 | Lindstrom |
| 3,565,804 A | 2/1971 | Honnen |
| 3,576,743 A | 4/1971 | Widmer |
| 3,630,904 A | 12/1971 | Musser |
| 3,632,511 A | 1/1972 | Liao |
| 3,755,433 A | 8/1973 | Miller |
| 3,804,763 A | 4/1974 | Meinhardt |
| 3,822,209 A | 7/1974 | Knapp |
| 3,857,791 A | 12/1974 | Marcellis et al. |
| 4,234,435 A | 11/1980 | Meinhardt et al. |
| 6,821,307 B2 | 11/2004 | Caprotti et al. |
| 7,112,230 B2 | 9/2006 | Malfer et al. |
| 7,491,248 B2 | 2/2009 | Colucci et al. |
| 2008/0052985 A1 | 3/2008 | Stevenson et al. |
| 2008/0113890 A1 | 5/2008 | Moreton et al. |
| 2008/0307698 A1 | 12/2008 | Barton et al. |
| 2011/0258917 A1 | 10/2011 | Garcia Castro et al. |
| 2011/0315107 A1 | 12/2011 | Grabarse et al. |
| 2012/0010112 A1 | 1/2012 | Grabarse et al. |
| 2013/0031827 A1 | 2/2013 | Reid et al. |
| 2014/0238328 A1* | 8/2014 | Fang | C10L 1/2222 123/1 A |
| 2017/0121621 A1* | 5/2017 | Fabre | C10L 1/22 |

FOREIGN PATENT DOCUMENTS

| | | | |
|---|---|---|---|
| GB | 1483199 A | 8/1977 | |
| GB | 1548253 A | 7/1979 | |
| GB | 2533892 A | 7/2016 | |
| GB | 2535253 A | 8/2016 | |
| RO | 88958 A | 4/1998 | |
| WO | 2001042399 A1 | 6/2001 | |
| WO | 2003078553 A2 | 9/2003 | |
| WO | 2006135881 A2 | 12/2006 | |
| WO | 2010078300 A | 7/2010 | |
| WO | 2011095819 A1 | 8/2011 | |
| WO | 2011143744 A8 | 11/2011 | |
| WO | 2013017889 A1 | 2/2013 | |
| WO | 2015011506 A1 | 1/2015 | |
| WO | 2015011507 A1 | 1/2015 | |
| WO | WO-2015011506 A1 * | 1/2015 | C08F 110/10 |
| WO | 2016016641 A1 | 2/2016 | |
| WO | 2017017454 A1 | 2/2017 | |

OTHER PUBLICATIONS

Combined Search and Examination Report issued in Application No. GB1805089.8 dated Nov. 8, 2018.

Search Report issued in Application No. GB1705089.9, dated Jan. 17, 2018.

Shanmugam, et al., "Design, Synthesis, and Characterization of Bismaleimide Co-Curing Elastomers" Ind. Eng. Chem. Res., 51, 26, 8957-8965, 2012.

* cited by examiner

COMPOSITION, METHOD AND USE

CROSS-REFERENCE TO RELATED APPLICATIONS

This application is a U.S. national stage application under 35 U.S.C. 371 of co-pending International Application No. PCT/GB2018/050846, filed on Mar. 28, 2018, and entitled COMPOSITION, METHOD AND USE, which in turn claims priority to and benefit of Great Britain Patent Application No. 1705089.9, filed Mar. 30, 2017, which is incorporated by reference herein in its entirety for all purposes.

This present invention relates to fuel compositions, methods and uses relating thereto. In particular, the invention relates to quaternary ammonium salt additives for fuel used in spark ignition engines.

With over a hundred years of development the spark ignition (SI) engine has become a highly tuned piece of engineering. As the SI engine has become more highly tuned it has become more sensitive to variations in its construction. The construction of such engines can change with use as deposits build up on certain components and through wear of other components. These changes in construction may not only change parameters such as power output and overall efficiency; they can also significantly alter the pollutant emissions produced. To try and minimise these time-related changes to an engine's construction fuel additives have been developed to minimise wear and deposit build-up phenomena. Examples include anti valve seat recession additives to reduce wear and detergents to reduce deposit build-up.

As engine technology has evolved so have the demands put upon fuel additive packages. Early gasoline detergents were formulated to overcome the problem of deposit build-up on carburettors. In a carburettor a partial vacuum in part of the engine intake system is used to draw fuel into the induction system. To provide better control of the fuel air mixture carburettors were replaced with fuel injection equipment where a pressure above atmospheric pressure was used to force the fuel into the intake system and to induce better atomisation of the fuel.

As a replacement for carburettors so called throttle body injectors were used with just a single injector taking the place of the carburettor. The position of a throttle body injector was thus very similar to that of the carburettor and the temperature regime was thus similar.

To obtain greater control over the fuel delivery into the engine cylinders there was a move to using individual fuel injectors for each cylinder. These injectors were thus placed in the individual inlet ports for each cylinder; this configuration thus became known as port fuel injection or PFI. Because the fuel injector was now placed closer to the combustion chamber it tended to get hotter. Also as it was closer to the engine inlet port it was more likely to be subjected to exhaust gases passing back into the inlet system during the initial part of the inlet valve opening event. This made the injector more prone to deposit build up and thus increased the demands on the fuel additive required to minimise this deposit build-up.

The systems so far outlined were designed to provide an air fuel mixture that was approximately stoichiometric. The engine power was determined by the amount of stoichiometric mixture provided to the cylinder. This was controlled by restricting the flow of mixture into the cylinders, known as throttling. This inevitably incurred pumping losses thus reducing the efficiency of the overall system.

To overcome this problem engine designers have developed injection systems where the fuel is injected directly into the cylinder. Such engines are alternatively known as direct injection spark ignition (DISI), direct injection gasoline (DIG), gasoline direct injection (GDI) etc. Injecting directly into the combustion chamber allows for some degree of stratification of the charge thus allowing an overall lean mixture whilst having a local rich or stoichiometric mixture to facilitate reliable combustion. This injection strategy however means that the fuel injector is subjected to higher temperatures and pressures. This increases the likelihood of forming deposits from the high temperature degradation of the fuel. The fact that the injector is in the combustion chamber also exposes the injector to combustion gases which may contain partially oxidised fuel and or soot particles which may accumulate, increasing the level of deposits. The ability to provide good atomisation of fuel and precise control of fuel flow rates and injection duration are critical to the optimum performance of these engine designs. The radically different operating environment of the fuel injector poses a whole new set of design constraints on the development of an effective fuel additive package. Mixture stratification can also result in combustion occurring in local rich regions leading to the formation of soot particles which can increase combustion chamber deposits. Because liquid fuel is injected into the combustion chamber there is a greater risk of liquid impingement on the combustion chamber surfaces, particularly the piston crown. Liquid fuel on the combustion chamber surfaces can undergo thermal decomposition leading to gum formation and thus increase the rate of build-up of combustion chamber deposits.

An additional problem arising from injecting the fuel directly into the combustion chamber is that fuel impingement on the inlet valves is significantly reduced. The use of fuel containing detergents was relied upon to remove the deposits that build up on the inlet valve tulip as a result of lubricating oil passing down the valve stem and from combustion gases passing back into the inlet system during the initial part of the inlet valve opening event. In a direct injection engine the only possibility for fuel to impinge on the inlet valve tulip is from early injection and late inlet valve closing. This therefore makes it extremely difficult for a fuel borne detergent to have a significant effect on inlet valve deposits.

Effective control of deposits in a direct injection spark ignition gasoline engine is, therefore, a challenging task. Knowledge gained in using additives in other contexts, for example in gasoline engines using carburettors or in gasoline engines using an individual, common, fuel injector, or fuel injectors in the inlet port of each cylinder, or in diesel engines, appear to be of little assistance in achieving effective control of deposits in a direct injection spark ignition gasoline engine.

The particular difficulties in achieving effective control of deposits in a direct injection spark ignition gasoline engine are known in the art. For example they are also explained in WO 01/42399, U.S. Pat. Nos. 7,112,230, 7,491,248 and WO 03/78553.

Even though fuel compositions and additives have been proposed for controlling deposits in each of the regimes described above, such difficulties show that there is a continuing need for fuel compositions which are effective in either or both of direct injection spark ignition gasoline engines and/or spark ignition gasoline engines without direct injection.

Many different types of compounds are known in the art for use as detergent additives in fuel oil compositions, for the control of deposits in engines.

The present inventors have developed novel quaternary ammonium compounds that are useful as additives in fuel and lubricant compositions.

According to a first aspect of the present invention there is provided a quaternary ammonium compound of formula (I):

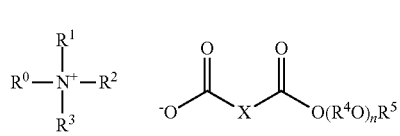

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

Preferably each of $R^0$, $R^1$, $R^2$ and $R^3$ is an optionally substituted alkyl, alkenyl or aryl group.

As used herein, the term "hydrocarbyl" substituent or group is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(i) hydrocarbon groups, that is, aliphatic (which may be saturated or unsaturated, linear or branched, e.g., alkyl or alkenyl), alicyclic (e.g., cycloalkyl, cycloalkenyl) substituents, and aromatic (including aliphatic- and alicyclic-substituted aromatic) substituents, as well as cyclic substituents wherein the ring is completed through another portion of the molecule (e.g., two substituents together form a ring);

(ii) substituted hydrocarbon groups, that is, substituents containing non-hydrocarbon groups (e.g., halo (especially chloro and fluoro), hydroxy, alkoxy, keto, acyl, cyano, mercapto, alkylmercapto, amino, alkylamino, nitro, nitroso, and sulphoxy);

(iii) hetero substituents, that is, substituents which, while having a predominantly hydrocarbon character, in the context of this invention, contain other than carbon in a ring or chain otherwise composed of carbon atoms. Heteroatoms include sulphur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

In this specification, unless otherwise stated references to optionally substituted alkyl groups may include aryl-substituted alkyl groups and references to optionally-substituted aryl groups may include alkyl-substituted or alkenyl-substituted aryl groups.

X is a linking group. Preferably X is an optionally substituted alkylene or arylene group. X is further defined herein.

The quaternary ammonium salt of the present invention may be prepared by any suitable means. Suitable methods will be known to the person skilled in the art.

In some embodiments, $R^0$ may be a lower alkyl group and the quaternary ammonium compound is prepared from an ester of formula $R^0OOCXCOO(R^4O)_nR^5$. In such embodiments $R^0$ is preferably methyl.

In some embodiments the quaternary ammonium salt may be prepared from an ester quaternising agent of formula $RCOOR^0$ followed by an ion exchange reaction with an acid of formula $HOOCXCOO(R^4O)_nR^5$. In such embodiments R may be an optionally substituted aryl or alkyl group or an ester. For example $R^0$ may be methyl and $RCOOR^0$ may be methyl salicylate or dimethyl oxalate.

In some embodiments $R^0$ is a C1 to C5 alkyl group, preferably methyl.

In preferred embodiments the quaternary ammonium compound is prepared from a tertiary amine, an acid-activated alkylating agent and an acid. Thus $R^0$ is preferably the residue of an alkylating agent.

In preferred embodiments the first aspect of the present invention provides a quaternary ammonium compound which is the reaction product of:
(a) a tertiary amine of formula $R^1R^2R^3N$;
(b) an acid-activated alkylating agent; and
(c) a compound of formula $HOOCXCOO—(R^4O)_n—R^5$ wherein $R^4$ is an optionally substituted alkylene group, $R^5$ is hydrogen or an optionally substituted alkyl, alkenyl or aryl group and n is 0 or a positive integer, provided that n is not 0 when $R^5$ is hydrogen.

According to a second aspect of the present invention there is provided a method of preparing a quaternary ammonium salt, the method comprising reacting (a) a tertiary amine of formula $R^1R^2R^3N$ with (b) an acid-derived alkylating agent in the presence of (c) a compound of formula $HOOCXCOO—(R^4O)_n—R^5$, wherein $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

Preferred features of the first and second aspects of the invention will now be described.

In this specification any feature of any aspect of the invention may be combined with any feature of any other aspect as appropriate.

X is a linking group. Preferably X is an optionally substituted alkylene or arylene group. X is further defined herein.

The present invention relates to a composition, a method and a use involving a quaternary ammonium salt. This compound may be referred to herein as "the quaternary ammonium salt" or as "the quaternary ammonium compound".

The quaternary ammonium salt may comprise a single compound. In some embodiments mixtures containing more than one quaternary ammonium salt additive may be used.

References herein to "a quaternary ammonium salt" of the invention or "the quaternary ammonium salt" include mixtures comprising two or more such compounds.

Component (a) used to prepare the quaternary ammonium salts of the present invention is a tertiary amine. Any suitable tertiary amine may be used.

In some embodiments of the present invention the tertiary amine may be a small compound of low complexity and low molecular weight. In some embodiments the tertiary amine may be a complex molecule and/or a molecule of high molecular weight which includes a tertiary amine moiety.

The tertiary amine compounds of the present invention preferably do not include any primary or secondary amine groups. In some embodiments they may be derived from compounds including these groups but preferably these have been subsequently reacted to form additional tertiary amine species. The tertiary amine compound used as component (a) may contain more than one tertiary amine group. However tertiary amine compounds including primary or secondary amine groups are within the scope of the invention provided these groups do not prevent quaternisation of the tertiary amine species.

Tertiary amines for use herein are preferably compounds of formula $R^1R^2R^3N$, wherein each of $R^1$, $R^2$ and $R^3$ is independently an optionally substituted alkyl, alkenyl or aryl group.

$R^1$, $R^2$ and $R^3$ may be the same or different. In some preferred embodiments $R^1$ and $R^2$ are the same and $R^3$ is different.

Preferably each of $R^1$ and $R^2$ is independently an optionally substituted alkyl, alkenyl or aryl group having from 1 to 50 carbon atoms, preferably from 1 to 40 carbon atoms, more preferably from 1 to 30 carbon atoms.

Each of $R^1$ and $R^2$ may be optionally substituted with one or more groups selected from halo (especially chloro and fluoro), hydroxy, alkoxy, keto, acyl, cyano, mercapto, alkylmercapto, dialkylamino, nitro, nitroso, and sulphoxy. The alkyl groups of these substituents may be further substituted.

Preferably each of $R^1$ and $R^2$ is independently an optionally substituted alkyl or alkenyl group. Preferably each of $R^1$ and $R^2$ is independently an optionally substituted alkyl group. Preferably each of $R^1$ and $R^2$ is independently an optionally substituted alkyl or alkenyl group having from 1 to 50 carbon atoms, preferably from 1 to 40 carbon atoms, more preferably from 1 to 30 carbon atoms, suitably from 1 to 20 carbon atoms, preferably from 1 to 12 carbon atoms, more preferably from 1 to 10 carbon atoms, suitably from 1 to 8 carbon atoms, for example from 1 to 6 carbon atoms.

In some embodiments each of $R^1$ and $R^2$ is methyl and $R^3$ is a $C_6$ to $C_{36}$, preferably a $C_{10}$ to $C_{30}$, alkyl or alkenyl group.

In some embodiments $R^1$ is methyl and each of $R^2$ and $R^3$ is a $C_6$ and $C_{36}$, preferably a $C_{10}$ to $C_{30}$ alkyl or alkenyl group.

Preferably $R^1$ is an optionally substituted alkyl or alkenyl group, preferably having from 1 to 10, preferably from 1 to 4 carbon atoms. Preferably $R^1$ is an alkyl group. It may be a substituted alkyl group, for example a hydroxy substituted alkyl group. Preferably $R^1$ is an unsubstituted alkyl group. The alkyl chain may be straight-chained or branched. In some preferred embodiments $R^1$ is selected from methyl, ethyl, propyl and butyl, including isomers thereof. In some especially preferred embodiments $R^1$ is methyl or ethyl.

Preferably $R^2$ is an optionally substituted alkyl or alkenyl group, preferably having from 1 to 10, preferably from 1 to 4 carbon atoms. Preferably $R^2$ is an alkyl group. It may be a substituted alkyl group, for example a hydroxy substituted alkyl group. Preferably $R^2$ is an unsubstituted alkyl group. The alkyl chain may be straight-chained or branched. In some preferred embodiments $R^2$ is selected from methyl, ethyl, propyl and butyl, including isomers thereof. In some especially preferred embodiments $R^2$ is methyl or ethyl.

In some embodiments $R^3$ is an optionally substituted alkyl or alkenyl group having from 1 to 50 carbon atoms, preferably from 1 to 40 carbon atoms, more preferably from 1 to 30 carbon atoms, suitably from 1 to 20 carbon atoms, preferably from 1 to 12 carbon atoms, more preferably from 1 to 10 carbon atoms, suitably from 1 to 8 carbon atoms, for example from 1 to 6 carbon atoms. Suitable substituents include halo (especially chloro and fluoro), hydroxy, alkoxy, keto, acyl, cyano, mercapto, alkylmercapto, amino, alkylamino, nitro, nitroso, sulphoxy, amido, alkyamido, imido and alkylimido. The alkyl groups of these substituents may be further substituted.

In some embodiments $R^3$ is an optionally substituted alkyl or alkenyl group, preferably having from 1 to 10, preferably from 1 to 4 carbon atoms. Suitably $R^3$ is an optionally substituted alkyl group. In some embodiments $R^3$ is an unsubstituted alkyl group, for example a $C_1$ to $C_{10}$, suitably a $C_1$ to $C_6$ or a $C_1$ to $C_4$ alkyl group. The alkyl group may be straight chain or branched.

In some preferred embodiments $R^3$ is a substituted alkyl group. Preferred substituents include alkoxy and hydroxyl groups.

In some embodiments the alkyl chain may be interrupted by one or more heteroatoms, for example one or more oxygen atoms.

In some preferred embodiments $R^3$ is a hydroxyl-substituted alkyl group. The alkyl chain may be straight-chained or branched. In some especially preferred embodiments $R^3$ is a hydroxyethyl group.

In one embodiment $R^3$ is a hydroxyethyloxyethyl group.

In some embodiments each of $R^1$, $R^2$ and $R^3$ is independently selected from an alkyl or hydroxyalkyl group having 1 to 12, preferably 1 to 6, more preferably 1 to 4 carbon atoms.

In some embodiments trialkylamines and hydroxyalkyl diakyl amines are especially preferred.

In some embodiments $R^3$ is an optionally substituted hydrocarbyl group, for example an optionally substituted hydrocarbyl group having from 1 to 300 carbon atoms, for example from 1 to 200 carbon atoms. $R^3$ may be an optionally substituted hydrocarbyl group having a number average molecular weight of from 100 to 5000, preferably from 500 to 2500.

In some embodiments $R^3$ is an optionally substituted aryl group or alkaryl group. For example $R^3$ may be benzyl.

In some embodiments $R^3$ is an optionally substituted alkyl or alkenyl group. $R^3$ may be an In some embodiments $R^3$ is an optionally substituted alkyl or alkenyl group. $R^3$ may be an unsubstituted alkyl or alkenyl group. Suitably $R^3$ is an alkyl or alkenyl group having from 1 to 200 carbon atoms.

In some embodiments $R^3$ is an alkyl group or alkenyl group having 10 to 36 carbon atoms.

In some embodiments $R^3$ is a polyisobutenyl group, preferably a polyisobutenyl group having a molecular weight of from 100 to 5000, preferably from 300 to 4000, suitably from 450 to 2500, for example from 500 to 2000 or from 600 to 1500.

In some embodiments $R^3$ is an optionally substituted alkylene phenol moiety and the tertiary amine $R^1R^2R^3N$ is the product of a Mannich reaction between an aldehyde, an optionally substituted phenol and an amine. Suitably the aldehyde is formaldehyde. The amine used to prepare the Mannich compound may be a monoamine and $R^3$ would have the structure (A):

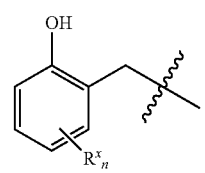

(A)

The amine used to prepare the Mannich compound may be a polyamine, including at least one tertiary amine group and $R^3$ may have the structure (B):

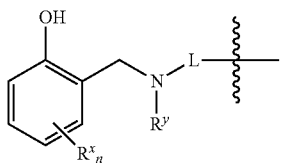

(B)

In structures (A) and (B) n is 0 to 4, preferably 1, $R^x$ is an optionally substituted hydrocarbyl group, $R^y$ is an optionally substituted alkyl, alkenyl or aryl group; and L is a linking group.

$R^y$ and L may together form a heterocyclic group.

$R^y$ is preferably an alkyl group, preferably an unsubstituted alkyl group. $R^y$ is suitably a $C_1$ to $C_4$ alkyl group.

Preferably L is an optionally substituted alkylene group, preferably an alkylene group having 1 to 10, preferably 1 to 6 carbon atoms. More preferably L is an unsubstituted alkylene group, for example ethylene, propylene or butylene. Most preferably L is a propylene group.

In some preferred embodiments, the phenol includes an ortho-methyl substituent and a further substituent $R^x$ at the para-position.

In a preferred embodiment, n is 1 and the optionally substituted hydrocarbyl substituent $R^x$ is preferably para to the hydroxyl group.

The optionally substituted hydrocarbyl substituent $R^x$ of the phenol can have 6 to 400 carbon atoms, suitably 30 to 180 carbon atoms, for example 10 or 40 to 110 carbon atoms. This hydrocarbyl substituent can be derived from an olefin or a polyolefin.

The polyolefins which can form the hydrocarbyl substituent can be prepared by polymerizing olefin monomers by well known polymerization methods and are also commercially available.

Some preferred polyolefins include polyisobutylenes having a number average molecular weight of 200 to 3000, in another instance of 400 to 2500, and in a further instance of 400 or 500 to 1500.

In some embodiments the phenol may include a lower molecular weight alkyl substituent for example a phenol which carries one or more alkyl chains having a total of less than 28 carbon atoms, preferably less than 20 carbon atoms, more preferably less than 14 carbon atoms.

A monoalkyl phenol may be preferred, suitably having from 4 to 20 carbons atoms, preferably 8 to 16 carbon atoms, for example a phenol having a $C_{12}$ alkyl substituent.

In some embodiments $R^3$ may include an ether, amide or ester group.

In some embodiments $R^3$ includes succinimide moiety. $R^3$ may have the formula:

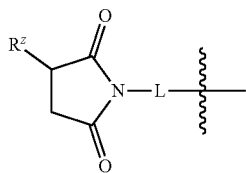

wherein $R^z$ is an optionally substituted hydrocarbyl group and L is a linking group.

In some embodiments the optionally substituted hydrocarbyl substituent $R^z$ can have 6 to 36 carbon atoms, preferably 8 to 22, for example 10 to 18 or 16 to 18 carbon atoms.

In some embodiments the optionally substituted hydrocarbyl substituent $R^z$ can have 6 to 400 carbon atoms, suitably 30 to 180 carbon atoms, for example 10 or 40 to 110 carbon atoms. This hydrocarbyl substituent can be derived from an olefin or a polyolefin.

Some preferred polyolefins include polyisobutylenes having a number average molecular weight of 200 to 3000, in another instance of 400 to 2500, and in a further instance of 400 or 500 to 1500.

Preferably L is an optionally substituted alkylene group, preferably an alkylene group having 1 to 10, preferably 1 to 6 carbon atoms. More preferably L is an unsubstituted alkylene group, for example ethylene, propylene or butylene. Most preferably L is a propylene group.

$R^3$ may suitably be selected from an optionally substituted alkyl or alkenyl group having 1 to 10 carbon atoms; an optionally substituted hydrocarbyl group having a molecular weight of 100 to 5000; an optionally substituted alkylene phenol moiety and an optionally substituted alkylene succinimide group.

Suitable tertiary amine compounds for use as component (a) include simple alkylamino and hydroxyalkylamino compounds; trialkylamino compounds having a high molecular weight substituent; Mannich reaction products including a tertiary amine and substituted acylated amines or alcohols including a tertiary amine.

Simple alkylamino and hydroxyalkyl amino compounds are preferably compounds of formula $R^1R^2R^3N$, wherein each of $R^1$, $R^2$ and $R^3$ is an alkyl group or a hydroxyalkyl group. Each of $R^1$, $R^2$ and $R^3$ may be the same or different. Suitably each of $R^1$, $R^2$ and $R^3$ is independently selected from an alkyl or hydroxyalkyl group having 1 to 10, preferably 1 to 6 carbon atoms, for example 1 to 4 carbon atoms. Each of $R^1$, $R^2$ and $R^3$ may be independently selected from methyl, ethyl, propyl, butyl, pentyl, hexyl, hydroxymethyl, hydroxyethyl, hydroxypropyl, hydroxybutyl, hydroxypentyl and hydroxyhexyl. Component (a) may be a trialkylamine, a dialkylhydroxyalkylamine, a dihydroxyalkylalkylamine or a trihydroxyalkylamine. There are many different compounds of this type and these will be known to the person skilled in the art.

In some embodiments the amine may include alkyl or hydroxyalkyl groups which have been reacted with an epoxide compound (for example ethylene oxide or propylene oxide) to provide an ether.

Trialkylamino compounds having a high molecular weight substituent suitable for use herein are typically polyalkene-substituted amines including at least one tertiary amino group.

The polyalkene-substituted amines having at least one tertiary amino group of the present invention may be derived from an olefin polymer and an amine, for example ammonia, monoamines, polyamines or mixtures thereof. They may be prepared by a variety of methods such as those described and referred to in US 2008/0113890.

Suitably the polyalkene substituent of the polyalkene-substituted amine is derived from a polyisobutylene.

The amines that can be used to make the polyalkene-substituted amine include ammonia, monoamines, polyamines, or mixtures thereof, including mixtures of different monoamines, mixtures of different polyamines, and mixtures of monoamines and polyamines (which include diamines). The amines include aliphatic, aromatic, heterocyclic and carbocyclic amines. Preferred amines are generally substituted with at least one hydrocarbyl group having 1 to about 50 carbon atoms, preferably 1 to 30 carbon atoms. Saturated aliphatic hydrocarbon radicals are particularly preferred.

The monoamines and polyamines suitably include at least one primary or secondary amine group.

The number average molecular weight of the polyalkene-substituted amines can range from 500 to 5000, or from 500 to 3000, for example from 1000 to 1500.

Any of the above polyalkene-substituted amines which are secondary or primary amines, may be alkylated to tertiary amines using alkylating agents. Suitable alkylating agents and methods using these will be known to the person skilled in the art.

Suitable Mannich reaction products having a tertiary amine for use as component (a) are described in US 2008/0052985.

The Mannich reaction product having a tertiary amine group is prepared from the reaction of an optionally substituted hydrocarbyl-substituted phenol, an aldehyde and an amine. The optionally substituted hydrocarbyl-substituted phenol is suitably as previously described herein.

Preferably the optionally substituted hydrocarbyl-substituted phenol is a polyisobutenyl-substituted phenol or a polyisobutenyl-substituted cresol.

The aldehyde used to form the Mannich detergent can have 1 to 10 carbon atoms, and is generally formaldehyde or a reactive equivalent thereof such as formalin or paraformaldehyde.

The amine used to form the Mannich detergent can be a monoamine or a polyamine.

Examples of monoamines and polyamines are known to the person skilled in the art.

Preferred polyamines are polyethylene polyamines.

In especially preferred embodiments the amine used to form the Mannich detergent comprises a diamine. Suitably it includes a primary or secondary amine which takes part in the Mannich reaction and in addition a tertiary amine.

One preferred amine is dimethylaminopropylamine.

In preferred embodiments the Mannich detergent is the product directly obtained from a Mannich reaction and comprising a tertiary amine. For example the amine may comprise a single primary or secondary amine which when reacted in the Mannich reaction forms a tertiary amine which is capable of being quaternised. Alternatively the amine may comprise a primary or secondary amine capable of taking part in the Mannich reaction and also a tertiary amine capable of being quaternised. However the Mannich detergent may comprise a compound which has been obtained from a Mannich reaction and subsequently reacted to form a tertiary amine, for example a Mannich reaction may yield a secondary amine which is then alkylated to form a tertiary amine.

Suitable preferred amines include dimethylamine and dibutylamine.

Substituted acylated amines or alcohols including a tertiary amine for use as component (a) include the reaction product of an optionally substituted hydrocarbyl-substituted acylating agent and a compound having an oxygen or nitrogen atom capable of condensing with said acylating agent and further having a tertiary amino group.

The optionally substituted hydrocarbyl substituted acylating agent is preferably a mono- or polycarboxylic acid (or reactive equivalent thereof) for example a substituted succinic, phthalic or propionic acid.

Preferred hydrocarbyl substituted acylating agents for use in the preparation of component (i) are polyisobutenyl substituted succinic acid derivatives. Preferred compounds are those having a polyisobutenyl group with a molecular weight of from 100 to 5000, preferably from 300 to 4000, suitably from 450 to 2500, for example from 500 to 2000 or from 600 to 1500.

In some preferred embodiments the tertiary amine comprises a compound formed by the reaction of an optionally substituted hydrocarbyl-substituted acylating agent and an amine of formula (II) or (III):

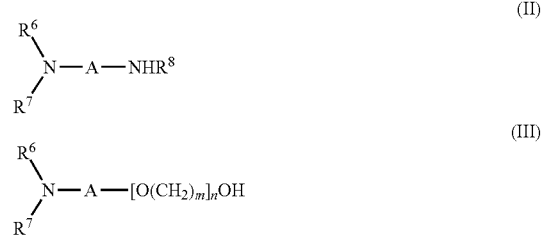

wherein $R^6$ and $R^7$ are the same or different alkyl, alkenyl or aryl groups having from 1 to 22 carbon atoms; A is a bond or is an alkylene group having from 1 to 20 carbon atoms; n is from 0 to 20; m is from 1 to 5; and $R^4$ is hydrogen or a $C_1$ to $C_{22}$ alkyl group.

The conditions of the above reaction are suitably selected to ensure that there are no free acid groups present in the tertiary amine component (a) that is formed. For example when a compound of formula (II) is reacted with a succinic acid derived acylating agent the reaction conditions or ratio of reactants are selected to ensure that the imide or diamide are formed. The monoamide is not formed. When a compound of formula (III) is reacted with a succinic acid derived acylating agent the reaction conditions or ratio of reactants are selected to ensure that the diester is formed. The monoester is not formed.

When a compound of formula (II) is used, $R^8$ is preferably hydrogen or a $C_1$ to $C_{18}$, suitably a $C_1$ to $C_{16}$ alkyl group. More preferably $R^8$ is selected from hydrogen, methyl, ethyl, propyl, butyl and isomers thereof. Most preferably $R^8$ is hydrogen.

When a compound of formula (III) is used, m is preferably 2 or 3, most preferably 2; n is preferably from 0 to 15, preferably 0 to 10, more preferably from 0 to 5. Most preferably n is 0 and the compound of formula (III) is an alcohol.

Preferably the optionally substituted hydrocarbyl substituted acylating agent is reacted with a diamine compound of formula (II).

$R^6$ and $R^7$ are the same or different alkyl, alkenyl or aryl groups having from 1 to 22 carbon atoms. In some embodiments $R^6$ and $R^7$ may be joined together to form a ring structure, for example a piperidine, imidazole or morpholine moiety. Thus $R^6$ and $R^7$ may together form an aromatic and/or heterocyclic moiety. $R^6$ and $R^7$ may be branched alkyl or alkenyl groups. Each may be substituted, for example with a hydroxy or alkoxy substituent.

Preferably each of $R^6$ and $R^7$ is independently a $C_1$ to $C_{16}$ alkyl group, preferably a $C_1$ to $C_{10}$ alkyl group. $R^6$ and $R^7$ may independently be methyl, ethyl, propyl, butyl, pentyl, hexyl, heptyl, octyl, or an isomer of any of these. Preferably $R^6$ and $R^7$ is each independently $C_1$ to $C_4$ alkyl. Preferably $R^6$ is methyl. Preferably $R^7$ is methyl.

A is a bond or alkylene group having from 1 to 20 carbon atoms. A is preferably an alkylene group having 1 to 12 carbon atoms, more preferably 1 to 8 carbon atoms, for example 2 to 6 carbon atoms or 2 to 5 carbon atoms. Most preferably A is an ethylene, propylene or butylene group, especially a propylene group.

Examples of compounds of formula (II) suitable for use herein will be known to the person skilled in the art.

In some preferred embodiments the compound of formula (II) is selected from dimethylaminopropylamine, N,N-diethyl-1,3-diaminopropane, N,N-dimethylethylenediamine, N,N-diethylethylenediamine, N,N-dibutylethylenediamine, or combinations thereof.

Examples of compounds of formula (III) suitable for use herein will be known to the person skilled in the art.

In some preferred embodiments the compound of formula (III) is selected from triisopropanolamine, 1-[2-hydroxyethyl]piperidine, 2-[2-(dimethylamine)ethoxy]-ethanol, N-ethyldiethanolamine, N-methyldiethanolamine, N-butyldiethanolamine, N,N-diethylaminoethanol, N,N-dimethylaminoethanol, 2-dimethylamino-2-methyl-1-propanol, or combinations thereof.

An especially preferred compound of formula (II) is dimethylaminopropylamine.

Further especially preferred tertiary amine compounds (a) are formed by the reaction of a compound including a primary amine group and a tertiary amine group and a polyisobutenyl-substituted succinic acid. One especially preferred amine compound having a primary and a tertiary amine group is dimethylaminopropylamine. The polyisobutenyl substituent preferably has a molecular weight of from 300 to 2500, suitably from 500 to 1500. Thus an especially preferred compound for use as component (a) is a polyisobutenyl-substituted succinimide prepared from dimethylaminopropylamine.

Preferred tertiary amine compounds for use as component (a) include N,N-dimethyl ethanolamine, dimethyloctadecylamine, N-methyl N,N-ditallowamine, N,N-diethyl ethanolamine, triethylamine, tripropylamine and tributylamine.

Especially preferred tertiary amines for use as component (a) include N, N-dimethylethanolamine, N, N-diethylethanolamine, triethylamine and tributylamine.

Other suitable amine that may be used as component (a) include small cyclic amines. These include for example compounds based on N-alkyl heterocycles, suitably selected from pyrolidine, piperidine, morpholine, piperazine, pyrrole, imidazole and dihydropyrrole, pyridine, pyrimidine, isoxansole and oxazole. Suitable amine starting materials of this type are described, for example, in the applicant's copending application PCT/GB2016/052312.

In some embodiments component (a) is selected from:
trialkyl amines in which each alkyl group has 1 to 6, preferably 1 to 4 carbons atoms;
dimethyl alkyl or alkenyl amines in which the alkyl or alkenyl group has 6 to 36, preferably 10 to 30 carbon atoms;
tertiary amines in which each substituent is selected from alkyl, hydroxyalkyl and hydroxyalkyloxyalkyl groups having 1 to 12, preferably 1 to 6 carbon atoms.

Preferred amines for use as component (a) are trialkylamines in which each alkyl group has 1 to 12, preferably 1 to 6 carbons atoms and in which each alkyl group may be hydroxyl substituted and/or substituted with an oxygen atom within the carbon chain.

Preferably component (a) is an amine of formula $R^1R^2R^3N$, wherein each of $R^1$, $R^2$ and $R^3$ is independently an unsubstituted alkyl group having 1 to 6 carbon atoms, a hydroxy substituted alkyl group having 1 to 6 carbon atoms or a hydroxyalkyloxyalkyl group having 1 to 6 carbon atoms.

By hydroxyalkyloxyalkyl group we mean a group of formula $HOR^aOR^b$ wherein each of $R^a$ and $R^b$ is an alkylene group. These may be formed by alkylation of a hydroxyalkyl substituent with an epoxide.

Most preferably component (a) is an amine of formula $R^1R^2R^3N$, wherein each of $R^1$, $R^2$ and $R^3$ is independently an unsubstituted alkyl group having 1 to 6 carbon atoms, or a hydroxy substituted alkyl group having 1 to 6 carbon atoms.

Component (b) used to prepare the quaternary ammonium compound of the present invention in preferred embodiments is an acid activated alkylating agent. Preferred acid-activated alkylating agents are epoxide compounds.

Any suitable epoxide compound may be used. Suitable epoxide compounds are those of formula:

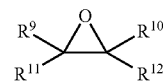

wherein each of $R^9$, $R^{10}$, $R^{11}$, $R^{12}$ is independently selected from hydrogen or an optionally substituted alkyl, alkenyl or aryl group.

In such embodiments $R^0$ as shown in formula (I) is thus suitably a group of formula:

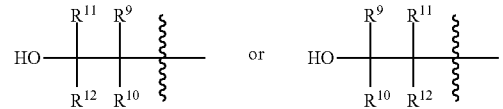

Preferably at least one of $R^9$, $R^{10}$, $R^{11}$ and $R^{12}$ is hydrogen. Preferably at least two of $R^9$, $R^{10}$, $R^{11}$ and $R^{12}$ are hydrogen. Most preferably three of $R^9$, $R^{10}$, $R^{11}$ and $R^{12}$ are hydrogen. $R^9$, $R^{10}$, $R^{11}$ and $R^{12}$ may be all hydrogen.

In the structure above and the definitions which follow $R^9$ and $R^{10}$ are interchangeable and thus when these groups are different either enantiomer or diastereomer may be used as component (b).

In the structure above and the definitions which follow $R^{11}$ and $R^{12}$ are interchangeable and thus when these groups are different either enantiomer or diastereomer may be used as component (b).

Preferably $R^9$ is hydrogen or an optionally substituted alkyl, alkenyl or aryl group, preferably having from 1 to 10, preferably from 1 to 4 carbon atoms. Preferably $R^9$ is hydrogen or an alkyl group. Most preferably $R^9$ is hydrogen.

Preferably $R^{10}$ is hydrogen or an optionally substituted alkyl, alkenyl or aryl group, preferably having from 1 to 10 carbon atoms. For example $R^{10}$ may be benzyl.

In some preferred embodiments $R^{10}$ is an optionally substituted aryl group. For example $R^{10}$ may be phenyl.

In some preferred embodiments $R^{10}$ is an optionally substituted alkyl or alkenyl group. Suitably $R^{10}$ is an alkyl group, for example an unsubstituted alkyl group. $R^{10}$ may be an alkyl group having 1 to 12, for example 1 to 8 or 1 to 4 carbon atoms.

Preferably $R^{10}$ is hydrogen or an alkyl group. Most preferably $R^{10}$ is hydrogen.

Preferably $R^{11}$ is hydrogen or an optionally substituted alkyl, alkenyl or aryl group, preferably having from 1 to 10, preferably from 1 to 4 carbon atoms. Preferably $R^{11}$ is hydrogen or an alkyl group. Most preferably $R^{11}$ is hydrogen.

Preferably $R^{12}$ is hydrogen or an optionally substituted alkyl, alkenyl or aryl group.

In some preferred embodiments $R^{12}$ is an optionally substituted aryl group. For example $R^{12}$ may be phenyl.

In some preferred embodiments $R^{12}$ is an optionally substituted alkyl or alkenyl group. $R^{12}$ may be an alkyl group, for example an unsubstituted alkyl group. $R^{12}$ may be an alkyl group having 1 to 50 carbon atoms, preferably from 1 to 30 carbon atoms, suitably 1 to 20 carbon atoms, preferably from 1 to 12 carbon atoms, for example from 1 to 8 or from 1 to 4 carbon atoms.

In some embodiments $R^{12}$ is an alkyl group having 6 to 20 carbon atoms, preferably from 8 to 16 carbon atoms.

In some embodiments $R^{12}$ is hydrogen.

In some preferred embodiments $R^{12}$ is the moiety $CH_2OR^{13}$ or $CH_2OCOR^{14}$ wherein each of $R^{13}$ and $R^{14}$ may be an optionally substituted alkyl, alkenyl or aryl group.

$R^{13}$ is preferably an optionally substituted alkyl or aryl group, preferably having from 1 to 30 carbon atoms, preferably from 1 to 20 carbon atoms, suitably from 1 to 12 carbon atoms. When $R^{13}$ is an alkyl group it may be straight-chained or branched. In some embodiments it is branched. $R^{13}$ may be an optionally substituted phenyl group.

In one embodiment $R^{13}$ is a 2-methyl phenyl group. In another embodiment $R^{13}$ is $CH_2C(CH_2CH_3)CH_2CH_2CH_2CH_3$.

$R^{14}$ may be an optionally substituted alkyl, alkenyl or aryl group.

$R^{14}$ is preferably an optionally substituted alkyl or aryl group, preferably having from 1 to 30 carbon atoms, preferably from 1 to 20 carbon atoms, suitably from 1 to 12 carbon atoms. When $R^{14}$ is an alkyl group it may be straight-chained or branched. In some preferred embodiments it is branched. $R^{14}$ may be an optionally substituted phenyl group.

In one embodiment $R^{14}$ is $C(CH_3)R_2$ wherein each R is an alkyl group. The R groups may be the same or different.

Component (b) is preferably an epoxide. The present invention therefore provides a quaternary ammonium compound which is the reaction product of:
(a) a tertiary amine of formula $R^1R^2R^3N$;
(b) an epoxide; and
(c) a compound of formula $HOOCXCOO(R^4O)R^5$ wherein $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

Preferred epoxide compounds for use as component (b) include styrene oxide, ethylene oxide, propylene oxide, butylene oxide, epoxyhexane, octene oxide, stilbene oxide and other alkyl and alkenyl epoxides having 2 to 50 carbon atoms.

Other suitable epoxide compounds include glycidyl ethers and glycidyl esters, for example gylcidyl 2 methyl phenyl ether and the glycidyl ester of versatic acid.

Suitably component (b) may be selected from styrene oxide, ethylene oxide, propylene oxide, butylene oxide, epoxyhexane, octene oxide, stilbene oxide, 2-ethylhexyl glycidyl ether, 1,2-epoxydodecane and other alkyl and alkenyl epoxides having 2 to 50 carbon atoms.

Preferably component (b) is selected from styrene oxide, propylene oxide, butylene oxide, and 2-ethylhexyl glycidyl ether.

More preferably component (b) is selected from propylene oxide, butylene oxide and 2-ethylhexyl glycidyl ether.

The quaternary ammonium salt of the present invention includes an anion of formula $-OOCXCOO(R^4O)_nR^5$.

Suitably the quaternary ammonium salt is prepared by reaction of (a) a quaternary amine; (b) an epoxide; and (c) an acid of formula $HOOCXCOO(R^4O)_nR^5$.

The compound of formula $HOOCXCOO(R^4O)_nR^5$ is suitably a half ester which is the reaction product of an optionally substituted dicarboxylic acid or anhydride thereof and an alcohol of formula $HO(R^4O)_nR^5$.

In some embodiments the dicarboxylic acid or anhydride is unsubstituted. In preferred embodiments the additive is prepared from a hydrocarbyl substituted dicarboxylic acid or an anhydride thereof.

Suitable dicarboxylic acids include maleic acid, glutaric acid, fumaric acid, oxalic acid, malonic acid, pimelic acid, suberic acid, adipic acid, phthalic acid, succinic acid, azelaic acid, sebacic acid and dimerised fatty acids.

In one embodiment component (c) is the reaction product of an optionally substituted polycarboxylic acid or anhydride thereof selected from pyromellitic acid, malonic acid, sebacic acid and succinic acid. Suitably component (c) is an optionally substituted succinic acid or an anhydride thereof.

In some embodiments the compound of formula $HOOCXCOO(R^4O)R^5$ (component (c)) is prepared from a dimerised fatty acid. Such compounds are formed from the dimerization of unsaturated fatty acids, for example unsaturated fatty acids having 6 to 50, suitably 8 to 40, preferably 10 to 36, for example 10 to 20 carbon atoms, or 16 to 20 carbon atoms.

Such dimerised fatty acids may have 12-100 carbon atoms, preferably 16-72 carbon atoms such as 20-40 carbon atoms for example 32-40 carbon atoms.

These compound are well known in the art, particularly for their use as corrosion inhibitors. Particularly preferred dimerised fatty acids are mixtures of C36 dimer acids such as those prepared by dimerising oleic acid, linoleic acid and mixtures comprising oleic and linoleic acid, for example, tall oil fatty acids.

The quaternary ammonium compound of formula (I) includes a linking group X. Preferably X includes a hydrocarbyl substituent. Preferably X is an optionally substituted arylene or alkylene group.

In some embodiments component (c) is prepared from phthalic acid or an anhydride thereof, having the formula (A1) or (A2):

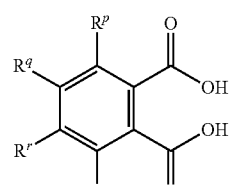

(A1)

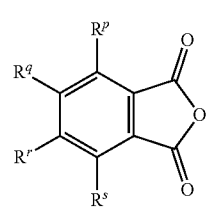

(A2)

wherein each of $R^p$, $R^q$, $R^r$ and $R^s$ is independently hydrogen or an optionally substituted hydrocarbyl group.

Preferably each is hydrogen or an optionally substituted alkyl or alkenyl group. Preferably three of $R^p$, $R^q$, $R^r$ and $R^s$ are hydrogen and the other is an optionally substituted $C_1$ to $C_{500}$ alkyl or alkenyl group, preferably a $C_2$ to $C_{100}$ alkyl or alkenyl group, preferably a $C_6$ to $C_{60}$ alkyl or alkenyl group, preferably a $C_8$ to $C_{40}$ alkyl or alkenyl group, more preferably a $C_{10}$ to $C_{36}$ alkyl or alkenyl group, preferably a $C_{12}$ to $C_{22}$ alkyl or alkenyl group, suitably a $C_{16}$ to $C_{28}$ alkyl or alkenyl group, for example a $C_{20}$ to $C_{24}$ alkyl or alkenyl group. The alkyl or alkenyl group may be straight chain or branched. Preferably $R^p$, $R^q$ and $R^s$ are hydrogen and $R^r$ is an optionally substituted alkyl or alkenyl group.

X in formula (I) is preferably an optionally substituted hydrocarbylene group. Preferably X is an optionally substituted alkylene group. Preferably X is a substituted alkylene group.

Suitably X is an alkyl or alkenyl substituted alkylene group.

Preferably X is an alkyl substituted alkylene group.

Preferably X is an alkyl substituted alkylene group wherein the alkylene group was 1 to 10, preferably 1 to 6, suitably 1 to 4, preferably 2 or 3, and most preferably 2 carbon atoms in the alkylene chain.

In some preferred embodiments X is $CH_2CHR$ or $CHRCH_2$ wherein R is an optionally substituted hydrocarbyl group.

Preferably component (c) used to prepare the quaternary ammonium salt of the present invention is the reaction product of an optionally substituted succinic acid or anhydride thereof of formula (A3) or (A4):

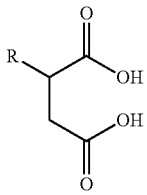

(A3)

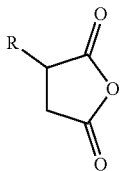

(A4)

wherein R is hydrogen or an optionally substituted hydrocarbyl group. Preferably $R^4$ is an optionally substituted alkyl or alkenyl group.

In some embodiments R is an optionally substituted $C_1$ to $C_{500}$ alkyl or alkenyl group, preferably a $C_2$ to $C_{100}$ alkyl or alkenyl group, preferably a $C_6$ to $C_{60}$ alkyl or alkenyl group, preferably a $C_8$ to $C_{40}$ alkyl or alkenyl group, more preferably a $C_{10}$ to $C_{38}$ alkyl or alkenyl group, preferably a $C_{16}$ to $C_{36}$ alkyl or alkenyl group, suitably a $C_{18}$ to $C_{32}$ alkyl or alkenyl group.

R may be substituted with one or more groups selected from halo (e.g. chloro, fluoro or bromo), nitro, hydroxy, mercapto, sulfoxy, amino, nitryl, acyl, carboxy, alkyl (e.g. $C_1$ to $C_4$ alkyl), alkoxyl (e.g. $C_1$ to $C_4$ alkoxy), amido, keto, sulfoxy and cyano.

Preferably R is an unsubstituted alkyl or alkenyl group. The substituted succinic acid or anhydrides may suitably be prepared by reacting maleic anhydride with an alkene.

In some embodiments the R has a molecular weight of from 100 to 5000, preferably from 300 to 4000, suitably from 450 to 2500, for example from 500 to 2000 or from 600 to 1500.

In some embodiments the substituted succinic acid or anhydride thereof may comprise a mixture of compounds including groups R of different lengths. In such embodiments any reference to the molecular weight of the group R relates to the number average molecular weight for the mixture.

In some embodiments R is a polyisobutenyl group, preferably having a number average molecular weight of from 100 to 5000, preferably from 200 to 2400, suitably from 220 to 1400.

In some embodiments R is a polyisobutenyl group having a number average molecular weight of from 400 to 700.

In some embodiments R is a polyisobutenyl group having a number average molecular weight of from 180 to 400.

In some embodiments R is a polyisobutenyl group having a number average molecular weight of from 800 to 1200.

In some embodiments R is an alkyl or alkenyl group having 6 to 40 carbon atoms, preferably 10 to 38 carbon atoms, more preferably 16 to 36 carbon atoms, suitably 18 to 26 carbon atoms, for example 20 to 24 carbon atoms.

In some embodiments R may be the residue of an internal olefin. In such embodiments the compound of formula (A3) or (A4) is suitably obtained by the reaction of maleic acid with an internal olefin.

An internal olefin as used herein means any olefin containing predominantly a non-alpha double bond that is a beta or higher olefin. Preferably such materials are substantially completely beta or higher olefins, for example containing less than 10% by weight alpha olefin, more preferably less than 5% by weight or less than 2% by weight. Typical internal olefins include Neodene 1518IO available from Shell.

Internal olefins are sometimes known as isomerised olefins and can be prepared from alpha olefins by a process of isomerisation known in the art, or are available from other sources. The fact that they are also known as internal olefins reflects that they do not necessarily have to be prepared by isomerisation.

Component (c) is the reaction product of a succinic acid or anhydride of formula (A3) or (A4) and an alcohol of formula $H$—$(OR^4)_n$—$OR^5$; wherein R is an alkyl or alkenyl group having 6 to 36 carbon atoms or a polyisobutenyl group having a number average molecular weight of from 200 to 1300.

In some especially preferred embodiments component (c) is prepared from a succinic acid or anhydride having a $C_{10}$ to $C_{30}$, preferably a $C_{20}$ to $C_{24}$ alkyl or alkenyl group.

Component (c) may have the formula (B1) or (B2):

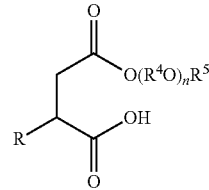

(B1)

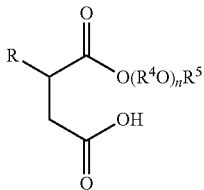
(B2)

Such a compound may be prepared by the reaction of a hydrocarbyl substituted succinic acid or anhydride with an alcohol of formula HO(R$^4$O)$_n$R$^5$.

Preferably the acid/anhydride and the alcohol are reacted in a molar ratio of from 10:1 to 1:10, preferably from 5:1 to 1:5, more preferably from 2:1 to 1:2, for example from 1.5:1 to 1:1.5.

Most preferably the acid/anhydride and the alcohol are reacted in an approximately 1:1 molar ratio, for example from 1.2:1 to 1:1.2.

Suitably n is from 0 to 30, preferably from 0 to 20, suitably from 1 to 16; R$^4$ is an alkylene group having 1 to 12, preferably 1 to 6, more preferably 2 or 3 carbon atoms; and R$^5$ is hydrogen or a C$_1$ to C$_{40}$, preferably a C$_6$ to C$_{30}$, more preferably a C$_{10}$ to C$_{20}$ alkyl group; provided n is not 0 when R$^5$ is hydrogen.

R$^5$ is an optionally substituted hydrocarbyl group.

In some embodiments n is 0 and the additive of the invention may be formed from an alcohol of formula R$^5$OH.

In such embodiments R$^5$ is suitably an optionally substituted alkyl, alkenyl or aryl group, preferably having from 1 to 60, preferably from 10 to 40 carbon atoms. Preferably R$^5$ is an optionally substituted alkyl group. In some embodiments R$^5$ is a hydroxy substituted alkyl group.

In some preferred embodiments R$^5$ is an unsubstituted alkyl group. The alkyl group may be straight chained or branched. In some embodiments R$^5$ is an optionally substituted alkyl group having 4 to 40, preferably 6 to 30, more preferably 10 to 20 carbon atoms.

In some embodiments n is 0 and component (c) is prepared from a C$_6$ to C$_{36}$, preferably a C$_8$ to C$_{30}$, more preferably a C$_{10}$ to C$_{20}$ optionally substituted alcohol.

In one embodiment component (c) is an ester of tetradecanol.

Suitable alcohols of formula R$^5$OH for use herein include benzyl alcohol, tetradecanol, butanol, 2-butanol, isobutanol, octanol, 2-ethylhexanol, hexanol, cyclohexanol, cyclooctanol, 2-propylheptanol, 2-ethyl-1-butanol and isopropanol.

Suitable alcohols of formula R$^5$OH for use herein are butanol and 2-ethylhexanol.

In some embodiments n is not 0 and the quaternary ammonium salt may suitably be formed from an alcohol of formula HO(R$^4$O)$_n$R$^5$.

R$^5$ is hydrogen or an optionally substituted hydrocarbyl group.

When R$^5$ is hydrogen component (c) is suitably an ester of an alkylene glycol or a polyalkylene glycol.

When R$^5$ is not hydrogen, component (c) may be formed by reaction of the optionally substituted dicarboxylic acid with an alkylene glycol or polyalkylene glycol which is subsequently reacted to form an ether or a compound of formula HO(R$^4$O)$_n$R$^5$ may be reacted with the optionally substituted dicarboxylic acid.

R$^4$ is an optionally substituted alkylene group.

In some embodiments the alcohol of formula H—(OR)$_n$—OH has more than 2 hydroxy groups and the group R is a hydroxyl substituted alkylene group. Such a group may have 1, 2 or more hydroxyl groups.

For example in some embodiments the alcohol H—(OR)$_n$—OH may be glycerol, penterythritol or trimethylolpropane.

Preferably R$^4$ is an unsubstituted alkylene group.

Preferably R$^4$ is an optionally substituted alkylene group having 1 to 50 carbon atoms, preferably 1 to 40 carbon atoms, preferably 1 to 30 carbon atoms, more preferably 1 to 20 carbon atoms, suitably 1 to 10 carbon atoms, for example 2 to 6 or 2 to 4 carbon atoms.

Preferably R$^4$ is an unsubstituted alkylene group having 1 to 50 carbon atoms, preferably 1 to 20, more preferably 1 to 10, suitably 2 to 6, for example 2 to 4 carbon atoms. R$^4$ may be straight chained or branched.

Suitably R$^4$ may be an ethylene, propylene, butylene, pentylene, or hexylene group. When R$^4$ has more than 2 carbon atoms any isomer may be present. Preferably R$^4$ is an ethylene or a propylene group, most preferably a propylene group.

In some embodiments in which n is 1, R$^4$ may be a group of formula (CH$_2$)$_x$ wherein x is from 2 to 12, preferably from 2 to 6.

In some embodiments in which n is 1, R$^4$ is a straight chain or branched alkylene group and the alcohol is selected from ethylene glycol, propylene glycol, 1,3-propanediol, 1,2-butanediol, 1,3-butanediol, 1,4-butanediol, 1,6-hexanediol and neopentyl glycol.

In some preferred embodiments R$^4$ is preferably CR$^a$R$^b$CR$^c$R$^d$ and the polyhydric alcohol has the formula H—(OCR$^a$R$^b$CR$^c$R$^d$)$_n$OH wherein each of R$^a$, R$^b$, R$^c$ and R$^d$ is independently hydrogen or an optionally substituted alkyl group. Preferably each R$^a$, R$^b$, R$^c$ and R$^d$ is independently selected from hydrogen or an optionally substituted alkyl group having 1 to 20, preferably 1 to 12, more preferably 1 to 4, for example 1 to 2 carbon atoms.

Preferably each of R$^a$, R$^b$, R$^c$ and R$^d$ is independently selected from hydrogen and an unsubstituted alkyl group, preferably having 1 to 20 carbon atoms, suitably 1 to 12 carbon atoms, preferably 1 to 4 atoms, for example 1 or 2 carbon atoms. Preferably at least two of R$^a$, R$^b$, R$^c$ and R$^d$ is hydrogen, more preferably at least three of R$^a$, R$^b$, R$^c$ and R$^d$ is hydrogen.

In some embodiments R$^a$, R$^b$, R$^c$ and R$^d$ are all hydrogen and R is an ethylene group CH$_2$CH$_2$.

In some embodiments three of R$^a$, R$^b$, R$^c$, and R$^d$ is hydrogen and the other is an unsubstituted alkyl group having 1 to 12, preferably 1 to 4, suitably 1 to 2, and most preferably 1 carbon atoms.

In some embodiments the polyhydric alcohols used to prepare component (c) are prepared from epoxides, preferably terminal epoxides.

R$^4$ may comprise a mixture of isomers. For example when R$^4$ is propylene, the polyhydric alcohol may include moieties —CH$_2$CH(CH$_3$)— and —CH(CH$_3$)CH$_2$— in any order within the chain.

R$^4$ may comprise a mixture of different groups for example ethylene, propylene or butylene units. Block copolymer units are preferred in such embodiments.

R$^4$ is preferably an ethylene, propylene or butylene group. R$^4$ may be an n-propylene or n-butylene group or an isopropylene or isobutylene group. For example R$^4$ may be —CH$_2$CH$_2$—, —CH$_2$CH(CH$_3$)—, —CH$_2$C(CH$_3$)$_2$, —CH(CH$_3$)CH(CH$_3$)— or —CH$_2$CH(CH$_2$CH$_3$)—.

Preferably R$^4$ is ethylene or propylene. More preferably R$^4$ is —CH$_2$CH$_2$— or —CH(CH$_3$)CH$_2$—. Most preferably R$^4$ is —CH(CH$_3$)CH$_2$—.

In some embodiments n is at least 1. Preferably n is from 1 to 100, preferably from 1 to 50, more preferably from 1 to 30, more preferably from 1 to 24, preferably from 1 to 20, suitably from 1 to 16, preferably from 1 to 14.

In some embodiments n is from 4 to 10, for example from 6 to 8.

In some embodiments n is from 1 to 6, suitably from 2 to 5, for example 3 or 4.

In some embodiments n is from 8 to 16, for example from 11 to 14.

In some embodiments component (c) is prepared from a polyhydric alcohol of formula $HO(R^4O)H$ or an ether thereof of formula $HO(R^4O)_nR^5$.

Preferably the acid/anhydride and the alcohol are reacted in a molar ratio of from 10:1 to 1:10, preferably from 5:1 to 1:5, more preferably from 2:1 to 1:2, for example from 1.5:1 to 1:1.5.

Most preferably the acid/anhydride and the alcohol are reacted in an approximately 1:1 molar ratio, for example from 1.2:1 to 1:1.2.

In some embodiments the polyhydric alcohol may be a polypropylene glycol having a number average molecular weight of 425.

In some embodiments the polyhydric alcohol may be selected from triethylene glycol, tetraethylene glycol, propylene glycol, dipropylene glycol and tripropylene glycol.

In some embodiments the polyhydric alcohol is selected from ethylene glycol, propylene glycol and oligomers or polymers thereof.

In some embodiments the polyhydric alcohol may be a polypropylene glycol having a number average molecular weight of 725.

The skilled person will appreciate that commercial sources of alcohols of formula $H-(OR^4)_n-OH$ will often contain mixtures of compounds, for example in which n may be between 6 and 10.

Commercial sources of substituted succinic acids and anhydrides may also contain mixtures of compounds, for example including different compounds with substituents having 20 to 24 carbon atoms.

In some preferred embodiments $R^5$ is hydrogen.

In some embodiments $R^5$ is hydrogen, n is 1, and R is a straight chain or branched alkylene group. In such embodiments the alcohol of formula $HO(R^4O)_nR^5$ is selected from ethylene glycol, propylene glycol, 1,3-propanediol, 1,2-butanediol, 1,3-butanediol, 1,4-butanediol, 1,6-hexanediol and neopentyl glycol.

In some embodiments $R^5$ is not hydrogen, n is not 0 and the additive of the invention is prepared from an ether of a polyhydric alcohol, for example an ether of a polyethylene glycol, a polypropylene glycol, triethylene glycol, tetraethylene glycol, propylene glycol, dipropylene glycol or tripropylene glycol.

In some embodiments in which n is not 0, $R^5$ is an optionally substituted alkyl, alkenyl or aryl group, suitably an optionally substituted alkyl or alkenyl group. Preferably $R^5$ has from 4 to 50 carbon atoms, preferably 4 to 40 carbon atoms, more preferably from 10 to 30 carbon atoms. $R^5$ may be straight chain or branched. Preferably $R^5$ is straight chain.

In some embodiments $R^5$ is a substituted alkyl or alkenyl group, suitably a substituted alkyl group. Suitably substituents are hydroxy and ester groups.

Suitably $R^5$ is an unsubstituted alkyl or alkenyl group. Preferably $R^5$ is an alkyl group, preferably an unsubstituted alkyl group.

Suitably $R^5$ is selected from hydrogen, and an alkyl group having from 1 to 40, preferably 6 to 30, more preferably 10 to 20 carbon atoms.

In some embodiments n is from 10 to 40, preferably 15 to 30, more preferably 20 to 25; $R^2$ is ethylene or propylene, most preferably propylene; and $R^5$ is a $C_6$ to $C_{30}$, preferably a $C_{10}$ to $C_{20}$ alkyl group.

In some embodiments component (c) used to prepare the quaternary ammonium salt of the present invention is the reaction product of a succinic acid or anhydride thereof having an alkyl or alkenyl substituent having 6 to 36 carbon atoms and a polypropylene glycol (or a $C_1$ to $C_{36}$ alkyl ether thereof) having a number average molecular weight of 300 to 800.

In some embodiments component (c) is the reaction product of a succinic acid or anhydride thereof having an alkyl or alkenyl substituent having 6 to 36 carbon atoms and a polyhydric alcohol (or a $C_1$ to $C_{36}$ alkyl ether thereof) selected from ethylene glycol, diethylene glycol, triethylene glycol, tetraethylene glycol, propylene glycol, dipropylene glycol, tripropylene glycol and tetrapropylene glycol.

In some embodiments component (c) is the reaction product of a succinic acid or anhydride thereof having an alkyl or alkenyl substituent having 6 to 36 carbon atoms and a polyhydric alcohol (or a $C_1$ to $C_{36}$ alkyl ether thereof) selected from glycerol, pentaerythritol and trimethylolpropane.

In some embodiments component (c) is the reaction product of a succinic acid or anhydride having a $C_6$ to $C_{36}$, preferably a $C_{10}$ to $C_{30}$, more preferably a $C_{20}$ to $C_{24}$ alkyl or alkenyl substituent and an alcohol of formula $R^5OH$ wherein $R^5$ is a $C_6$ to $C_{30}$, preferably a $C_{10}$ to $C_{20}$ alkyl group.

In some embodiments component (c) is the reaction product of an optionally substituted polycarboxylic acid or anhydride thereof selected from pyromellitic acid, malonic acid, sebacic acid and succinic acid; and an alcohol of formula $HO(R^4O)_nR^5$, the alcohol being selected from:
  ethylene glycol, propylene glycol and oligomers or polymers thereof; alkane diols having 1 to 12, preferably 3 to 6 carbon atoms, sugar alcohols or ethers thereof; and alkanols having 1 to 30, preferably 6 to 25 carbon atoms.

In some embodiments component (c) is the reaction product of an optionally substituted polycarboxylic acid or anhydride thereof selected from pyromellitic acid and succinic acid; and an alcohol of formula $HO(R^4O)_nR^5$ wherein the alcohol is selected from:
  ethylene glycol, diethylene glycol, triethylene glycol, tetraethylene glycol, propylene glycol, dipropylene glycol, tripropylene glycol, tetrapropylene glycol, trehalose, 1,3-propanediol, 1,2-butanediol, 1,3-butanediol, 1,4-butanediol, 1,6-hexanediol, neopentyl glycol, a polyethylene or polypropylene glycol having a number average molecular weight of 300 to 1200; or a C1 to C30 ether thereof; and
  benzyl alcohol, tetradecanol, butanol, 2-butanol, isobutanol, octanol, 2-ethylhexanol, hexanol, cyclohexanol, cyclooctanol, 2-propylheptanol, 2-ethyl-1-butanol and isopropanol.

In some embodiments component (c) is the reaction product of a succinic acid or anhydride of formula (A3) or (A4) and an alcohol of formula $HO(R^4O)_nR^5$; wherein $R^2$ is an alkyl or alkenyl group having 6 to 36 carbon atoms or a polyisobutenyl group having a number average molecular weight of from 200 to 1300; wherein the alcohol of formula $HO(R^4O)_nR^5$ is selected from:

ethylene glycol, diethylene glycol, triethylene glycol, tetraethylene glycol, propylene glycol, dipropylene glycol, tripropylene glycol, tetrapropylene glycol, trehalose, sorbitol, glycerol, pentaerythritol, trimethylolpropane, 1,3-propanediol, 1,2-butanediol, 1,3-butanediol, 1,4-butanediol, 1,6-hexanediol, neopentyl glycol, a polyethylene or polypropylene glycol having a number average molecular weight of 300 to 1200; or a C6 to C24 ether thereof; and benzyl alcohol, tetradecanol, butanol, 2-butanol, isobutanol, octanol, 2-ethylhexanol, hexanol, cyclohexanol, cyclooctanol, 2-propylheptanol, 2-ethyl-1-butanol and isopropanol.

In some embodiments component (c) is the reaction product of a succinic acid or anhydride thereof having an alkyl or alkenyl substituent having 6 to 36 carbon atoms and a polyethylene glycol (or a $C_1$ to $C_{36}$ alkyl ether thereof) having a number average molecular weight of 200 to 800.

In some embodiments component (c) is the reaction product of a succinic acid or anhydride having an alkyl or alkenyl substituent having 6 to 36 carbon atoms and a polyethylene or polypropylene glycol (or a $C_1$ to $C_{36}$ alkyl ether thereof) having 4 to 16, preferably 6 to 8 alkoxy groups.

In some embodiments component (c) is the reaction product of a polyisobutenyl substituted succinic acid or anhydride thereof having a PIB substituent with a number average molecular weight of 200 to 2500 and a polypropylene glycol (or a $C_1$ to $C_{36}$ alkyl ether thereof) having a number average molecular weight of 300 to 800.

In some embodiments component (c) is the reaction product of a polyisobutenyl substituted succinic acid or anhydride thereof having a PIB substituent with a number average molecular weight of 200 to 2500 and a polyhydric alcohol (or a $C_1$ to $C_{36}$ alkyl ether thereof) selected from ethylene glycol, diethylene glycol, triethylene glycol, tetraethylene glycol, propylene glycol, dipropylene glycol, tripropylene glycol and tetrapropylene glycol.

In some embodiments component (c) is the reaction product of a polyisobutenyl substituted succinic acid or anhydride thereof having a PIB substituent with a number average molecular weight of 200 to 2500 and a polyhydric alcohol (or a $C_1$ to $C_{36}$ alkyl ether thereof) selected from glycerol, pentaerythritol and trimethylolpropane.

In some embodiments component (c) is a the reaction product of polyisobutenyl substituted succinic acid or anhydride thereof having a PIB substituent with a number average molecular weight of 200 to 2500 and a polyethylene glycol (or a $C_1$ to $C_{36}$ alkyl ether thereof) having a number average molecular weight of 200 to 800.

In some embodiments component (c) is the reaction product of a polyisobutenyl substituted succinic acid or anhydride thereof having a PIB substituent with a number average molecular weight of 200 to 2500 a polyethylene or polypropylene glycol (or a $C_1$ to $C_{36}$ alkyl ether thereof) having 4 to 16, preferably 6 to 8 alkoxy groups.

For avoidance of doubt component (c) may comprise a mixture of compounds. Compounds that may be present include mixtures formed by reacting a mixture of different polyhydric alcohols with a polycarboxylic acid and/or mixtures formed by reacting a polyhydric alcohol with a mixture of polycarboxylic acids and/or compounds formed by reacting a mixture of polyhydric alcohols with a mixture of carboxylic acids. Such mixtures may also include mixtures of initially pure fully formed ester compounds.

In an especially preferred embodiment component (c) is the reaction product of a succinic acid or anhydride having a $C_{20}$ to $C_{24}$ alkyl or alkenyl substituent and an alcohol selected from polypropylene glycol having a number average molecular weight of 300 to 800, 2-ethylhexanol and butanol.

In preferred embodiments the quaternary ammonium compound of the present invention is the reaction product of:
(a) a tertiary amine of formula $R^1R^2R^3N$ wherein each of, $R^1$, $R^2$ and $R^3$ is independently an optionally substituted alkyl group having 1 to 12 carbon atoms;
(b) an epoxide selected from styrene oxide, ethylene oxide, propylene oxide, butylene oxide, epoxyhexane, octene oxide, stilbene oxide, 2-ethylhexyl glycidyl ether, 1,2-epoxydodecane and other alkyl and alkenyl epoxides having 2 to 50 carbon atoms; and
(c) a compound of formula HOOCXCOO—$(R^4O)_n$—$R^5$ wherein X is $CH_2CHR$ or $CHRCH_2$ wherein R is an optionally substituted hydrocarbyl group; and
n is more than 1, $R^4$ is an ethylene or propylene group and $R^5$ is hydrogen; or
n is 0 or and $R^5$ is a C1 to C20 alkyl group.

In more preferred embodiments the quaternary ammonium compound of the present invention is the reaction product of:
(a) a tertiary amine of formula $R^1R^2R^3N$ wherein each of, $R^1$, $R^2$ and $R^3$ is independently an alkyl or hydroxyalkyl group having 1 to 6 carbon atoms;
(b) an epoxide selected from propylene oxide, butylene oxide and 2-ethylhexyl glycidyl ether; and
(c) a compound of formula HOOCXCOO—$(R^4O)_n$—$R^5$ which is the reaction product of a succinic acid or anhydride having a $C_{20}$ to $C_{24}$ alkyl or alkenyl substituent and an alcohol selected from polypropylene glycol having a number average molecular weight of 300 to 800, 2-ethylhexanol and butanol.

According to a third aspect of the present invention there is provided a composition comprising a quaternary ammonium compound of formula (I):

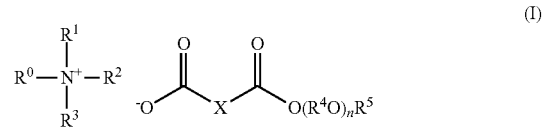

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

Preferred features of the third aspect are as defined in relation to the first and second aspects.

In some embodiments the composition of the third aspect is an additive composition comprising a quaternary ammonium salt of the first aspect and a diluent or carrier.

The additive composition may be an additive composition for lubricating oil.

Preferably the additive composition is an additive composition for a fuel composition, preferably a gasoline fuel composition.

The quaternary ammonium compound is suitably present in the additive composition in an amount of from 1 to 99 wt %, for example from 1 to 75 wt %.

The additive composition may comprise a mixture of two or more quaternary ammonium compounds of the present invention. In such embodiments the above amounts suitably refer to the total amount of all such compounds present in the composition.

The additive composition may include one or more further additives. These may be selected from further detergents, dispersants, anti-oxidants, anti-icing agents, metal deactivators, lubricity additives, friction modifiers, dehazers, corrosion inhibitors, dyes, markers, octane improvers, anti-valve-seat recession additives, stabilisers, demulsifiers, antifoams, odour masks, conductivity improvers and combustion improvers.

In some preferred embodiments the additive composition includes one or more further nitrogen-containing detergents.

The third aspect of the present invention may provide a fuel or lubricating oil composition comprising a quaternary ammonium salt of the first aspect.

In some embodiments the present invention provides a lubricating composition comprising an oil of lubricating viscosity and as an additive a quaternary ammonium salt of formula (I):

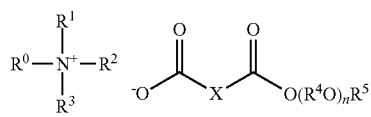

(I)

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

In some preferred embodiments the third aspect of the present invention provides a fuel composition comprising as an additive a quaternary ammonium salt of formula (I):

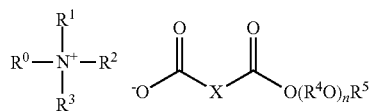

(I)

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

The present invention may further provide a method of preparing a fuel composition, the method comprising preparing a quaternary ammonium salt of the first aspect, and mixing the quaternary ammonium salt into the fuel.

The fuel composition of the present is preferably a gasoline fuel composition.

Suitably the quaternary ammonium salt additive is present in the gasoline fuel composition in an amount of at least 0.1 ppm, preferably at least 1 ppm, more preferably at least 5 ppm, suitably at least 10 ppm, preferably at least 20 ppm, for example at least 30 ppm or at least 50 ppm.

Suitably the quaternary ammonium salt additive is present in the gasoline fuel composition in an amount of less than 10000 ppm, preferably less than 1000 ppm, preferably less than 500 ppm, preferably less than 300 ppm, for example less than 250 ppm.

In some embodiments the quaternary ammonium salt additive is present in the gasoline fuel composition in an amount of suitably less than 200 ppm, for example less than 150 ppm.

Suitably the quaternary ammonium salt additive is present in the gasoline fuel in an amount of from 80 to 130 ppm.

In this specification any reference to ppm is to parts per million by weight.

The gasoline fuel compositions of the present invention may comprise a mixture of two or more quaternary ammonium salt additives. In such embodiments the above amounts refer to the total amounts of all such additives present in the composition.

The use of mixtures may arise due to the availability of starting materials or a particular mixture may be deliberately selected to use in order to achieve a benefit. For example, a particular mixture may lead to improvements in handling, a general improvement in performance or a synergistic improvement in performance.

In this specification any reference to "an additive" or "the additive" of the invention includes embodiments in which a single additive compound is present and embodiments in which two or more additive compounds are present. In embodiments in which two or more compounds are present the mixtures may be present due to a mixture of starting materials being used to prepare the additive compounds (e.g. a mixture of polyhydric alcohols and/or a mixture of polycarboxylic acids and/or a mixture of tertiary amines and/or a mixture of quaternising agents). Alternatively and/or additionally two or more pre-formed compounds of formula (I) may be mixed into a composition, for example a fuel or lubricating composition.

The quaternary ammonium salt additives may be added to gasoline fuel at any convenient place in the supply chain. For example, the additives may be added to fuel at the refinery, at a distribution terminal or after the fuel has left the distribution terminal. If the additive is added to the fuel after it has left the distribution terminal, this is termed an aftermarket application. Aftermarket applications include such circumstances as adding the additive to the fuel in the delivery tanker, directly to a customer's bulk storage tank, or directly to the end user's vehicle tank. Aftermarket applications may include supplying the fuel additive in small bottles suitable for direct addition to fuel storage tanks or vehicle tanks.

The present invention relates to a gasoline fuel composition.

By the term "gasoline", it is meant a liquid fuel for use with spark ignition engines (typically or preferably containing primarily or only C4-C12 hydrocarbons) and satisfying international gasoline specifications, such as ASTM D-439 and EN228. The term includes blends of distillate hydrocarbon fuels with oxygenated components such as alcohols or ethers for example methanol, ethanol, butanol, methyl t-butyl ether (MTBE), ethyl t-butyl ether (ETBE), as well as the distillate fuels themselves.

In some preferred embodiments, the quaternary ammonium salt additives of the invention may be used without additional components. In other preferred embodiments, the quaternary ammonium salt additive (i) is used with one or more additional components (ii) selected from:

a) carrier oils
b) acylated nitrogen compounds which are the reaction product of a carboxylic acid-derived acylating agent and an amine
c) hydrocarbyl-substituted amines wherein the hydrocarbyl substituent is substantially aliphatic and contains at least 8 carbon atoms
d) mannich base additives comprising nitrogen-containing condensates of a phenol, aldehyde and primary or secondary amine
e) aromatic esters of a polyalkylphenoxyalkanol
f) additional quaternary ammonium salts.

Preferably the ratio of the quaternary ammonium salt additive (i) to additional components (ii) when present, is 1:100 to 100:1, preferably 1:50:50:1, preferably 1:15 to 20:1 preferably 1:15 to 10:1 preferably 1:10 to 10:1 preferably 1:5 to 5:1.

Preferably the ratio of the quaternary ammonium salt additive (i) to carrier oil a) when present, is 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

Preferably the ratio of the quaternary ammonium salt additive (i) to acylated nitrogen additive b) 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

Preferably the ratio of the quaternary ammonium salt additive (i) to hydrocarbyl substituted amine c) 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

Preferably the ratio of the quaternary ammonium salt additive (i) to mannich base additives d) when present, is 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

Preferably the ratio of the quaternary ammonium salt additive (i) to aromatic ester e) when present, is 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

Preferably the ratio of the quaternary ammonium salt additive (i) to quaternary ammonium salt f) when present, is 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

Preferably the ratio of the total of the quaternary ammonium salt additive (i) and components b), c), d) and e) to carrier oil a) when present, is 1:100 to 100:1, preferably 1:50:50:1, preferably 1:15 to 20:1 preferably 1:15 to 10:1 preferably 1:10 to 10:1 preferably 1:5 to 5:1, preferably 1:2 to 2:1.

All ratios are weight ratios on an active basis. The total amount of compound(s) (i) and each compound a)-f) specified in the respective definition is to be taken into account.

a) Carrier Oil

The carrier oil may have any suitable molecular weight. A preferred molecular weight is in the range 500 to 5000.

In one embodiment the carrier oil may comprise an oil of lubricating viscosity. The oil of lubricating viscosity includes natural or synthetic oils of lubricating viscosity, oil derived from hydrocracking, hydrogenation, hydrofinishing, unrefined, refined and re-refined oils, or mixtures thereof. In one embodiment, the oil of lubricating viscosity is a carrier fluid for the dispersant and/or other performance additives.

Natural oils include animal oils, vegetable oils, mineral oils or mixtures thereof. Synthetic oils include a hydrocarbon oil, a silicon-based oil, a liquid ester of phosphorus-containing acid. Synthetic oils may be produced by Fischer-Tropsch reactions and typically may be hydroisomerised Fischer-Tropsch hydrocarbons or waxes.

Oils of lubricating viscosity may also be defined as specified in the American Petroleum Institute (API) Base Oil Interchangeability Guidelines. In one embodiment the oil of lubricating viscosity comprises an API Group I, II, III, IV, V or mixtures thereof, and in another embodiment API Group I, II, III or mixtures thereof.

In another embodiment the carrier oil may comprise a polyether carrier oil.

In a preferred aspect the polyether carrier oil is a mono end-capped polyalkylene glycol. Preferably the end cap is a group consisting of or containing a hydrocarbyl group having up to 30 carbon atoms. More preferably the end cap is or comprises an alkyl group having from 4 to 20 carbon atoms or from 12 to 18 carbon atoms.

The alkyl group may be branched or straight chain. Preferably it is a straight chain group.

Further hydrocarbyl end capping groups include alkyl-substituted phenyl, especially where the alkyl substituent(s) is or are alkyl groups of 4 to 20 carbon atoms, preferably 8 to 12, preferably straight chain.

The hydrocarbyl end capping group may be attached to the polyether via a linker group. Suitable end cap linker groups include an ether oxygen atom (—O—), an amine group (—NH—), an amide group (—CONH—), or a carbonyl group —(C=O)—.

Such end capped polyalkyleneglycols are obtainable by the polymerisation of $C_2$-$C_6$ alkylene oxides either as homopolymers or copolymers containing 4-100 repeat units. Copolymers may be random copolymers or block copolymers.

In a preferred aspect the polyether carrier oil is a mono end-capped polypropylene glycol.

In a preferred embodiment the carrier oil is a polyalkyleneglycol monoether of the formula:

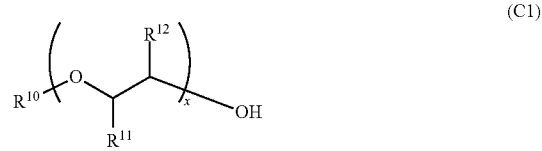

(C1)

where $R^{10}$ is a hydrocarbyl group having from 1 to 30 carbon atoms; $R^{11}$ and $R^{12}$ are each independently hydrogen or lower alkyl having from about 1 to about 6 carbon atoms and each $R^{11}$ and $R^{12}$ is independently selected in each —O—$CHR^{11}$—$CHR^{12}$-unit; and x is an integer of from 5 to 100, preferably 10 to 50, preferably 10 to 30, preferably 10-25, more preferably 12 to 25, more preferably 12 to 20.

In a preferred embodiment $R^{10}$ is a straight chain $C_1$-$C_{30}$ alkyl, preferably $C_4$-$C_{20}$ alkyl, preferably $C_8$-$C_{18}$ alkyl, and more preferably $C_{12}$-$C_{18}$ alkyl or $C_8$-$C_{14}$ alkyl.

In another preferred embodiment $R^{10}$ is an alkylphenyl group preferably an alkylphenyl group, wherein the alkyl moiety is a straight or branched chain alkyl of from about 1 to about 24 carbon atoms.

Preferably, one of $R^{11}$ and $R^{12}$ is lower alkyl of 1 to 4 carbon atoms, and the other is hydrogen. More preferably, one of $R^{11}$ and $R^{12}$ is methyl or ethyl, and the other is hydrogen.

In a preferred embodiment the carrier oil is a polypropyleneglycol monoether of the formula:

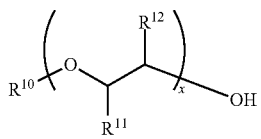

(C2)

where $R^{10}$, $R^{11}$, $R^{12}$ and x are as defined for (C1) above, and in each repeat unit one of $R^{11}$ and $R^{12}$ are hydrogen and the other is methyl.

Such alkyl polypropyleneglycol monoethers are obtainable by the polymerisation of propylene oxide using an aliphatic alcohol, preferably a straight chain primary alcohol of up to 20 carbon atoms, as an initiator. If desired a proportion of the propyleneoxy units, for example up to 50% of the propyleneoxy units by weight, may be replaced by units derived from other $C_2$-$C_6$ alkylene oxides, e.g. ethylene oxide or isobutylene oxide, and are to be included within the term "polypropyleneglycol". Alternatively, the initiator may be a phenol, alkyl phenol, a hydrocarbyl amine or amide, containing 1-30 carbon atoms, preferably a saturated aliphatic or aromatic hydrocarbyl group such as alkyl, phenyl or phenalkyl etc. Preferred initiators include long chain alkanols giving rise to the long chain polypropyleneglycol monoalkyl ethers.

In a further aspect the polyalkyleneglycol may be an ester. In this aspect the carrier oil may be a polypropyleneglycol monoester of the formula

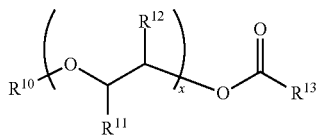

(C3)

where $R^{10}$, $R^{11}$, $R^{12}$ and x are as defined for (C1) above and $R^{13}$ is a $C_1$-$C_{30}$ hydrocarbyl group, preferably an aliphatic hydrocarbyl group, and more preferably $C_1$-$C_{10}$ alkyl.

In another embodiment a polyetheramine may be present.

It is known to those skilled in the art that the class of compounds known as polyetheramines function as deposit control additives. It is common for polyetheramines to be used as detergents and/or as carrier oils. For the purpose of this specification polyetheramines are classed herein as carrier oils.

Suitable hydrocarbyl-substituted polyoxyalkylene amines or polyetheramines employed in the present invention are described in the literature (for example U.S. Pat. Nos. 6,217,624 and 4,288,612) and have the general formula:

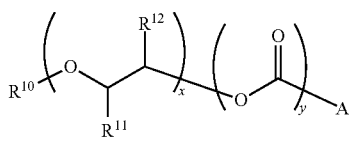

(C4)

or a fuel-soluble salt thereof; $R^{10}$, $R^{11}$, $R^{12}$ and x are as defined for (C1) above; A is amino, N-alkyl amino having about 1 to about 20 carbon atoms in the alkyl group, N,N-dialkyl amino having about 1 to about 20 carbon atoms in each alkyl group, or a polyamine moiety having about 2 to about 12 amine nitrogen atoms and about 2 to about 40 carbon atoms; and y is 0 or 1.

In general, A is amino, N-alkyl amino having from about 1 to about 20 carbon atoms in the alkyl group, preferably about 1 to about 6 carbon atoms, more preferably about 1 to about 4 carbon atoms; N,N-dialkyl amino having from about 1 to about 20 carbon atoms in each alkyl group, preferably about 1 to about 6 carbon atoms, more preferably about 1 to about 4 carbon atoms; or a polyamine moiety having from about 2 to about 12 amine nitrogen atoms and from about 2 to about 40 carbon atoms, preferably about 2 to 12 amine nitrogen atoms and about 2 to 24 carbon atoms. More preferably, A is amino or a polyamine moiety derived from a (poly)alkylene polyamine, including alkylene diamine. Most preferably, A is amino or a polyamine moiety derived from ethylene diamine or diethylene triamine.

The polyetheramines will generally have a molecular weight in the range from about 600 to about 10,000.

Fuel-soluble salts of the compounds of formula I can be readily prepared for those compounds containing an amino or substituted amino group and such salts are contemplated to be useful for preventing or controlling engine deposits. Suitable salts include, for example, those obtained by protonating the amino moiety with a strong organic acid, such as an alkyl- or arylsulfonic acid. Preferred salts are derived from toluenesulfonic acid and methanesulfonic acid.

Other suitable polyetheramines are those taught in U.S. Pat. Nos. 5,089,029 and 5,112,364.

b) Acylated Nitrogen Compounds which are the Reaction Product of a Carboxylic Acid-Derived Acylating Agent and an Amine The carboxylic derived acylating agent may be a hydrocarbyl substituted acylating agent as described for the quaternary ammonium salt(s) (i).

Amines useful for reaction with these acylating agents include the following:

(1) (Poly)alkylene polyamines of the general formula:

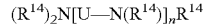

wherein each $R^{14}$ is independently selected from a hydrogen atom, a hydrocarbyl group or a hydroxy-substituted hydrocarbyl group containing up to about 30 carbon atoms, with proviso that at least one $R^{14}$ is a hydrogen atom, n is a whole number from 1 to 10 and U is a C1-18 alkylene group. Preferably each $R^{14}$ is independently selected from hydrogen, methyl, ethyl, propyl, isopropyl, butyl and isomers thereof. Most preferably each $R^{14}$ is ethyl or hydrogen. U is preferably a C1-4 alkylene group, most preferably ethylene.

Specific examples of (poly)alkylene polyamines (1) include ethylenediamine, diethylenetriamine, triethylenetetramine, tetraethylenepentamine, tri(tri-methylene)tetramine, pentaethylenehexamine, hexaethylene-heptamine, 1,2-propylenediamine, and other commercially available materials which comprise complex mixtures of polyamines. For example, higher ethylene polyamines optionally containing all or some of the above in addition to higher boiling fractions containing 8 or more nitrogen atoms etc.

Specific examples of (poly)alkylene polyamines (1) which are hydroxyalkyl-substituted polyamines include N-(2-hydroxyethyl) ethylene diamine, N,N'-bis(2-hydroxyethyl) ethylene diamine, N-(3-hydroxybutyl) tetramethylene diamine, etc.

(2) Heterocyclic-substituted polyamines

Suitable compounds of this type include hydroxyalkyl-substituted polyamines wherein the polyamines are as described above and the heterocyclic substituent is selected from nitrogen-containing aliphatic and aromatic heterocycles, for example piperazines, imidazolines, pyrimidines, morpholines, etc.

Specific examples of the heterocyclic-substituted polyamines (2) are N-2-aminoethyl piperazine, N-2 and N-3 amino propyl morpholine, N-3(dimethyl amino) propyl piperazine, 2-heptyl-3-(2-aminopropyl) imidazoline, 1,4-bis (2-aminoethyl) piperazine, 1-(2-hydroxy ethyl) piperazine, and 2-heptadecyl-1-(2-hydroxyethyl)-imidazoline, etc.

(3) Aromatic polyamines of the general formula:

wherein Ar is an aromatic nucleus of 6 to 20 carbon atoms, each $R^{15}$ is as defined above and y is from 2 to 8.

Specific examples of the aromatic polyamines (3) are the various isomeric phenylene diamines, the various isomeric naphthalene diamines, etc.

(4) The amine reactant may alternatively be a compound of general formula $R^{16}R^{17}NH$ where each of $R^{16}$ and $R^{17}$ independently represents a hydrocarbyl group (as defined herein), preferably a hydrocarbon group (as defined herein), or a hydrogen atom.

Preferably at least one of $R^{16}$ and $R^{17}$ represents a hydrocarbyl group.

Preferably both $R^{16}$ and $R^{17}$ represent a hydrocarbyl group.

Suitable terminal groups of a hydrocarbyl group $R^{16}$ and/or $R^{17}$ may include $-CH_3$, $=CH_2$, $-OH$, $-C(O)OH$ and derivatives thereof. Suitable derivatives include esters and ethers. Preferably a hydrocarbyl group $R^{16}$ and/or $R^{17}$ does not contain a terminal amine.

A preferred hydrocarbyl group for each of $R^{16}$ and $R^{17}$ is a group of the formula

wherein $R^{18}$ is an alkylene group having from 1 to 10 carbons, preferably from 1 to 5, preferably 1 to 3 carbons, preferably 2 carbons;

wherein $R^{19}$ is an alkylene group having from 1 to 10 carbons, preferably from 1 to 5, preferably 1 to 3 carbons, preferably 2 carbons;

wherein p is an integer from 0 to 10;

wherein X is selected from $-CH_3$, $-CH_2=CH_2$, $-OH$, and $-C(O)OH$.

A preferred hydrocarbyl group for each of $R^{16}$ and $R^{17}$ is a group of the formula

wherein p is an integer from 0 to 10, preferably 1 to 10, preferably from 1 to 5, preferably from 1 to 3, preferably 1 or 2;

wherein q is an integer from 1 to 10, preferably 1 to 10, preferably from 1 to 5, preferably from 1 to 3, preferably 1 or 2;

wherein r is an integer from 1 to 10, preferably 1 to 10, preferably from 1 to 5, preferably from 1 to 3, preferably 1 or 2; and wherein X is selected from $-CH_3$, $-CH_2=CH_2$, $-OH$, and $-C(O)OH$.

Preferably X is $-CH_3$, or $-OH$.

Further amines which may be used to prepare the acylated nitrogen compounds (b) include compounds derived from amines selected from ammonia, alkyamines e.g. butylamine, aminoethylethanolamine, aminopropan-2-ol, 5-aminopentan-1-ol, 2-(2-aminoethoxy)ethanol, monoethanolamine, 3-aminopropan-1-ol, 2-((3-aminopropyl)amino)ethanol, dimethylaminopropylamine, and N-(alkoxyalkyl)-alkanediamines including N-(octyloxyethyl)-1,2-diaminoethane and N-(decyloxypropyl)-N-methyl-1,3-diaminopropane.

Specific examples of amines which may be used in this invention and having a tertiary amino group can include but are not limited to: N,N-dimethyl-aminopropylamine, N,N-diethyl-aminopropylamine, N,N-dimethyl-amino ethylamine. The nitrogen or oxygen containing compounds capable of condensing with the acylating agent and further having a tertiary amino group can further include amino alkyl substituted heterocyclic compounds such as 1-(3-aminopropyl) imidazole and 4-(3-aminopropyl)morpholine, 1-(2-aminoethyl)piperidine, 3,3-diamino-N-methyldi-propylamine, and 3'3-aminobis(N,N-dimethylpropylamine). Other types of compounds capable of condensing with the acylating agent and having a tertiary amino group include alkanolamines including but not limited to triethanolamine, trimethanolamine, N,N-dimethylaminopropanol, N,N-diethylaminopropanol, N,N-diethylaminobutanol, N,N,N-tris(hydroxyethyl)amine and N,N,N-tris(hydroxymethyl)amine.

Many patents have described useful acylated nitrogen compounds including U.S. Pat. Nos. 3,172,892; 3,219,666; 3,272,746; 3,310,492; 3,341,542; 3,444,170; 3,455,831; 3,455,832; 3,576,743; 3,630,904; 3,632,511; 3,804,763, 4,234,435 and 6,821,307.

A preferred acylated nitrogen compound of this class is that made by reacting a poly(isobutene)-substituted succinic acid-derived acylating agent (e.g., anhydride, acid, ester, etc.) wherein the poly(isobutene) substituent has between about 12 to about 200 carbon atoms and the acylating agent has from 1 to 5, preferably from 1 to 3, preferably 1 or 2, succinic-derived acylating groups; with a mixture of ethylene polyamines having 3 to about 9 amino nitrogen atoms, preferably about 3 to about 8 nitrogen atoms, per ethylene polyamine and about 1 to about 8 ethylene groups. These acylated nitrogen compounds are formed by the reaction of a molar ratio of acylating agent:amino compound of from 10:1 to 1:10, preferably from 5:1 to 1:5, more preferably from 2.5:1 to 1:2, more preferably from 2:1 to 1:2 and most preferably from 2:1 to 1:1. In especially preferred embodiments, the acylated nitrogen compounds are formed by the reaction of acylating agent to amino compound in a molar ratio of from 1.8:1 to 1:1.2, preferably from 1.6:1 to 1:1.2, more preferably from 1.4:1 to 1:1.1 and most preferably from 1.2:1 to 1:1. This type of acylated amino compound and the preparation thereof is well known to those skilled in the art and are described in the above-referenced US patents. In other especially preferred embodiments, the acylated nitrogen compounds are formed by the reaction of acylating agent to amino compound in a molar ratio of from 2.5:1 to 1.5:1, preferably from 2.2:1 to 1.8:1.

Another type of acylated nitrogen compound belonging to this class is that made by reacting the afore-described alkylene amines with the afore-described substituted succinic acids or anhydrides and aliphatic mono-carboxylic acids having from 2 to about 22 carbon atoms. In these types of acylated nitrogen compounds, the mole ratio of succinic acid to mono-carboxylic acid ranges from about 1:0.1 to about 1:1. Typical of the monocarboxylic acid are formic acid, acetic acid, dodecanoic acid, butanoic acid, oleic acid, stearic acid, the commercial mixture of stearic acid isomers known as isostearic acid, tolyl acid, etc. Such materials are more fully described in U.S. Pat. Nos. 3,216,936 and 3,250, 715.

A further type of acylated nitrogen compound belonging to this class is the product of the reaction of a fatty monocarboxylic acid of about 12-30 carbon atoms and the afore-described alkylene amines, typically, ethylene, propylene or trimethylene polyamines containing 2 to 8 amino groups and mixtures thereof. The fatty mono-carboxylic acids are generally mixtures of straight and branched chain fatty carboxylic acids containing 12-30 carbon atoms. Fatty dicarboxylic acids could also be used. A widely used type of acylated nitrogen compound is made by reacting the afore-described alkylene polyamines with a mixture of fatty acids having from 5 to about 30 mole percent straight chain acid and about 70 to about 95 percent mole branched chain fatty acids. Among the commercially available mixtures are those known widely in the trade as isostearic acid. These mixtures are produced as a by-product from the dimerization of unsaturated fatty acids as described in U.S. Pat. Nos. 2,812, 342 and 3,260,671.

The branched chain fatty acids can also include those in which the branch may not be alkyl in nature, for example phenyl and cyclohexyl stearic acid and the chloro-stearic acids. Branched chain fatty carboxylic acid/alkylene polyamine products have been described extensively in the art. See for example, U.S. Pat. Nos. 3,110,673; 3,251,853; 3,326,801; 3,337,459; 3,405,064; 3,429,674; 3,468,639; 3,857,791. These patents are referenced for their disclosure of fatty acid/polyamine condensates for their use in lubricating oil formulations.

Suitably the molar ratio of the acylating group of an acylating agent defined above and the reacting amine group of said amine is in the range 0.5-5:1, preferably 0.8-2.2:1. At a ratio of 1:1 the reaction product is called mono-PIBSI, and at a ratio of 2:1 it is called bis-PIBSI and requires a polyamine as reactant.

Preferred acylated nitrogen compounds for use herein include: the compound formed by reacting a polyisobutylene succinic anhydride (PIBSA) having a PIB molecular weight of 900 to 1100, for example approximately 1000 with aminoethyl ethanolamine or triethylene tetramine; and the compound formed by reacting a PIBSA having a PIB molecular weight of 650 to 850, for example about 750 with tetraethylene pentamine. In each case the ratio of PIBSA to amine is from 1.5:1 to 0.9:1, preferably from 1.2:1 to 1:1. Other preferred acylated nitrogen compounds for use herein include: the compound formed by reacting a polyisobutylene succinic anhydride (PIBSA) having a PIB molecular weight of 900 to 1100, for example approximately 1000 with tetraethylene pentamine, the ratio of PIBSA to amine being from 2.5:1 to 1.5:1, preferably from 2.2:1 to 1.8:1.

c) Hydrocarbyl-Substituted Amines

Hydrocarbyl-substituted amines suitable for use in the present invention are well known to those skilled in the art and are described in a number of patents. Among these are U.S. Pat. Nos. 3,275,554; 3,438,757; 3,454,555; 3,565,804; 3,755,433 and 3,822,209. These patents describe suitable hydrocarbyl amines for use in the present invention including their method of preparation.

d) Mannich Additives

The Mannich additives comprise nitrogen-containing condensates of a phenol, aldehyde and primary or secondary amine Mannich additives can be made by reacting simultaneously or sequentially at least one of each of the following: active hydrogen compound for example a hydrocarbon-substituted phenol (e.g., an alkyl phenol wherein the alkyl group has at least an average of about 8 to 200; preferably at least 12 up to about 200 carbon atoms), having at least one hydrogen atom bonded to an aromatic carbon, with at least one aldehyde or aldehyde-producing material (typically formaldehyde or a precursor thereof) and an amine.

Thus the Mannich additives may be the product of a Mannich reaction between:

(a1) an aldehyde;
(b1) an amine; and
(c1) an optionally substituted phenol.

These compounds may be hereinafter referred to as "the Mannich additives". Thus in some preferred embodiments the present invention provides a gasoline composition comprising a quaternary ammonium salt(s) additive (i) and a Mannich additive.

Any aldehyde may be used as aldehyde component (a1) of the Mannich additive. Preferably the aldehyde component (a1) is an aliphatic aldehyde. Preferably the aldehyde has 1 to 10 carbon atoms, preferably 1 to 6 carbon atoms, more preferably 1 to 3 carbon atoms. Most preferably the aldehyde is formaldehyde.

Amine component (b1) may be at least one amino or polyamino compound having at least one NH group. The amino compounds include primary or secondary monoamines having hydrocarbon substituents of 1 to 30 carbon atoms or hydroxyl-substituted hydrocarbon substituents of 1 to about 30 carbon atoms.

In a preferred embodiment, the amine component (b1) is a polyamine.

Polyamines may be selected from any compound including two or more amine groups. Preferably the polyamine is a (poly)alkylene polyamine (by which is meant an alkylene polyamine or a polyalkylene polyamine; including in each case a diamine, within the meaning of "polyamine"). Preferably the polyamine is a (poly)alkylene polyamine in which the alkylene component has 1 to 6, preferably 1 to 4, most preferably 2 to 3 carbon atoms. Most preferably the polyamine is a (poly) ethylene polyamine (that is, an ethylene polyamine or a polyethylene polyamine).

Preferably the polyamine has 2 to 15 nitrogen atoms, preferably 2 to 10 nitrogen atoms, more preferably 2 to 8 nitrogen atoms.

Preferably the polyamine component (b1) includes the moiety $R^{21}R^{22}NCHR^{23}CHR^{24}NR^{25}R^{26}$ wherein each of $R^{21}$, $R^{22}$, $R^{23}$, $R^{24}$, $R^{25}$ and $R^{26}$ is independently selected from hydrogen, and an optionally substituted alkyl, alkenyl, alkynyl, aryl, alkylaryl or arylalkyl substituent.

Thus the polyamine reactants used to make the Mannich reaction products of the present invention preferably include an optionally substituted ethylene diamine residue.

Preferably at least one of $R^{21}$ and $R^{22}$ is hydrogen. Preferably both of $R^{21}$ and $R^{22}$ are hydrogen.

Preferably at least two of $R^{21}$, $R^{22}$, $R^{25}$ and $R^{26}$ are hydrogen.

Preferably at least one of $R^{23}$ and $R^{24}$ is hydrogen. In some preferred embodiments each of $R^{23}$ and $R^{24}$ is hydrogen. In some embodiments $R^{23}$ is hydrogen and $R^{24}$ is alkyl, for example $C_1$ to $C_4$ alkyl, especially methyl.

Preferably at least one of $R^{25}$ and $R^{26}$ is an optionally substituted alkyl, alkenyl, alkynyl, aryl, alkylaryl or arylalkyl substituent.

In embodiments in which at least one of $R^{21}$, $R^{22}$, $R^{23}$, $R^{24}$, $R^{25}$ and $R^{26}$ is not hydrogen, each is independently selected from an optionally substituted alkyl, alkenyl, alkynyl, aryl, alkylaryl or arylalkyl moiety. Preferably each is independently selected from hydrogen and an optionally substituted C(1-6) alkyl moiety.

In particularly preferred compounds each of $R^{21}$, $R^{22}$, $R^{23}$, $R^{24}$ and $R^{25}$ is hydrogen and $R^{26}$ is an optionally substituted alkyl, alkenyl, alkynyl, aryl, alkylaryl or arylalkyl substituent. Preferably $R^{26}$ is an optionally substituted C(1-6) alkyl moiety.

Such an alkyl moiety may be substituted with one or more groups selected from hydroxyl, amino (especially unsubstituted amino; —NH—, —NH$_2$), sulpho, sulphoxy, C(1-4) alkoxy, nitro, halo (especially chloro or fluoro) and mercapto.

There may be one or more heteroatoms incorporated into the alkyl chain, for example O, N or S, to provide an ether, amine or thioether.

Especially preferred substituents $R^{21}$, $R^{22}$, $R^{23}$, $R^{24}$, $R^{25}$ or $R^{26}$ are hydroxy-C(1-4)alkyl and amino-(C(1-4)alkyl, especially HO—CH$_2$—CH$_2$— and H$_2$N—CH$_2$—CH$_2$—.

Suitably the polyamine includes only amine functionality, or amine and alcohol functionalities.

The polyamine may, for example, be selected from ethylenediamine, diethylenetriamine, triethylenetetramine, tetraethylenepentamine, pentaethylene-hexamine, hexaethyleneheptamine, heptaethyleneoctamine, propane-1,2-diamine, 2(2-amino-ethylamino)ethanol, and N',N'-bis(2-aminoethyl) ethylenediamine (N(CH$_2$CH$_2$NH$_2$)$_3$). Most preferably the polyamine comprises tetraethylenepentamine or ethylenediamine.

Commercially available sources of polyamines typically contain mixtures of isomers and/or oligomers, and products prepared from these commercially available mixtures fall within the scope of the present invention.

The polyamines used to form the Mannich additives of the present invention may be straight chained or branched, and may include cyclic structures.

In preferred embodiments, the Mannich additives of the present invention are of relatively low molecular weight.

Preferably molecules of the Mannich additive product have a number average molecular weight of less than 10000, preferably less than 7500, preferably less than 2000, more preferably less than 1500.

Optionally substituted phenol component (c1) may be substituted with 0 to 4 groups on the aromatic ring (in addition to the phenol OH). For example it may be a tri- or di-substituted phenol. Most preferably component (c1) is a mono-substituted phenol. Substitution may be at the ortho, and/or meta, and/or para position(s).

Each phenol moiety may be ortho, meta or para substituted with the aldehyde/amine residue. Compounds in which the aldehyde residue is ortho or para substituted are most commonly formed. Mixtures of compounds may result. In preferred embodiments the starting phenol is para substituted and thus the ortho substituted product results.

The phenol may be substituted with any common group, for example one or more of an alkyl group, an alkenyl group, an alkyl group, a nitryl group, a carboxylic acid, an ester, an ether, an alkoxy group, a halo group, a further hydroxyl group, a mercapto group, an alkyl mercapto group, an alkyl sulphoxy group, a sulphoxy group, an aryl group, an arylalkyl group, a substituted or unsubstituted amine group or a nitro group.

Preferably the phenol carries one or more optionally substituted alkyl substituents. The alkyl substituent may be optionally substituted with, for example, hydroxyl, halo, (especially chloro and fluoro), alkoxy, alkyl, mercapto, alkyl sulphoxy, aryl or amino residues. Preferably the alkyl group consists essentially of carbon and hydrogen atoms. The substituted phenol may include a alkenyl or alkynyl residue including one or more double and/or triple bonds. Most preferably the component (c1) is an alkyl substituted phenol group in which the alkyl chain is saturated. The alkyl chain may be linear or branched.

Preferably component (c1) is a monoalkyl phenol, especially a para-substituted monoalkyl phenol.

Preferably component (c1) comprises an alkyl substituted phenol in which the phenol carries one or more alkyl chains having a total of less 28 carbon atoms, preferably less than 24 carbon atoms, more preferably less than 20 carbon atoms, preferably less than 18 carbon atoms, preferably less than 16 carbon atoms and most preferably less than 14 carbon atoms.

Preferably the or each alkyl substituent of component (c1) has from 4 to 20 carbons atoms, preferably 6 to 18, more preferably 8 to 16, especially 10 to 14 carbon atoms. In a particularly preferred embodiment, component (c1) is a phenol having a C12 alkyl substituent.

Preferably the or each substituent of phenol component (c1) has a molecular weight of less than 400, preferably less than 350, preferably less than 300, more preferably less than 250 and most preferably less than 200. The or each substituent of phenol component (c) may suitably have a molecular weight of from 100 to 250, for example 150 to 200.

Molecules of component (c1) preferably have a molecular weight on average of less than 1800, preferably less than 800, preferably less than 500, more preferably less than 450, preferably less than 400, preferably less than 350, more preferably less than 325, preferably less than 300 and most preferably less than 275.

Components (a1), (b1) and (c1) may each comprise a mixture of compounds and/or a mixture of isomers.

The Mannich additive is preferably the reaction product obtained by reacting components (a1), (b1) and (c1) in a molar ratio of from 5:1:5 to 0.1:1:0.1, more preferably from 3:1:3 to 0.5:1:0.5.

To form the Mannich additive of the present invention components (a1) and (b1) are preferably reacted in a molar ratio of from 6:1 to 1:4 (aldehyde:polyamine), preferably from 4:1 to 1:2, more preferably from 3:1 to 1:1.

To form a preferred Mannich additive of the present invention the molar ratio of component (a1) to component (c1) (aldehyde:phenol) in the reaction mixture is preferably from 5:1 to 1:4, preferably from 3:1 to 1:2, for example from 1.5:1 to 1:1.1.

Some preferred compounds used in the present invention are typically formed by reacting components (a1), (b1) and (c1) in a molar ratio of 2 parts (a1) to 1 part (b1)±0.2 parts (b1), to 2 parts (c1)±0.4 parts (c1); preferably approximately 2:1:2 (a1:b1:c1).

Some preferred compounds used in the present invention are typically formed by reacting components (a1), (b1) and (c1) in a molar ratio of 2 parts (a1) to 1 part (b1)±0.2 parts (b1), to 1.5 parts (c1)±0.3 parts (c1); preferably approximately 2:1:1.5 (a1:b1:c1).

Suitable treat rates of the quaternary ammonium salt(s) additive (i) and when present the Mannich additive will depend on the desired performance and on the type of engine in which they are used. For example different levels of additive may be needed to achieve different levels of performance.

e) Aromatic Esters of a Polyalkylphenoxyalkanol

The aromatic ester component which may be employed additive composition is an aromatic ester of a polyalkylphenoxyalkanol and has the following general formula:

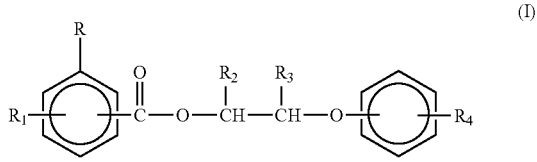

(I)

or a fuel-soluble salt(s) thereof wherein R is hydroxy, nitro or —(CH2)x-NR$_5$R$_6$, wherein R$_5$ and R$_6$ are independently hydrogen or lower alkyl having 1 to 6 carbon atoms and x is 0 or 1;

R$_1$ is hydrogen, hydroxy, nitro or —NR$_7$R$_5$ wherein R$_7$ and R$_5$ are independently hydrogen or lower alkyl having 1 to 6 carbon atoms;

R$_2$ and R$_3$ are independently hydrogen or lower alkyl having 1 to 6 carbon atoms; and R$_4$ is a polyalkyl group having an average molecular weight in the range of about 450 to 5,000.

The preferred aromatic ester compounds employed in the present invention are those wherein R is nitro, amino, N-alkylamino, or —CH$_2$NH$_2$ (aminomethyl). More preferably, R is a nitro, amino or —CH$_2$NH$_2$ group. Most preferably, R is an amino or —CH$_2$NH$_2$ group, especially amino. Preferably, R$_1$ is hydrogen, hydroxy, nitro or amino. More preferably, R$_1$ is hydrogen or hydroxy. Most preferably, R$_1$ is hydrogen. Preferably, R$_4$ is a polyalkyl group having an average molecular weight in the range of about 500 to 3,000, more preferably about 700 to 3,000, and most preferably about 900 to 2,500. Preferably, the compound has a combination of preferred substituents.

Preferably, one of R$_2$ and R$_3$ is hydrogen or lower alkyl of 1 to 4 carbon atoms, and the other is hydrogen. More preferably, one of R$_2$ and R$_3$ is hydrogen, methyl or ethyl, and the other is hydrogen. Most preferably, R$_2$ is hydrogen, methyl or ethyl, and R$_3$ is hydrogen.

When R and/or R$_1$ is an N-alkylamino group, the alkyl group of the N-alkylamino moiety preferably contains 1 to 4 carbon atoms. More preferably, the N-alkylamino is N-methylamino or N-ethylamino.

Similarly, when R and/or R$_1$ is an N,N-dialkylamino group, each alkyl group of the N,N-dialkylamino moiety preferably contains 1 to 4 carbon atoms. More preferably, each alkyl group is either methyl or ethyl. For example, particularly preferred N,N-dialkylamino groups are N,N-dimethylamino, N-ethyl-N-methylamino and N,N-diethylamino groups.

A further preferred group of compounds are those wherein R is amino, nitro, or —CH$_2$NH$_2$ and R$_1$ is hydrogen or hydroxy. A particularly preferred group of compounds are those wherein R is amino, R$_1$, R$_2$ and R$_3$ are hydrogen, and R$_4$ is a polyalkyl group derived from polyisobutene.

It is preferred that the R substituent is located at the meta or, more preferably, the para position of the benzoic acid moiety, i.e. para or meta relative to the carbonyloxy group. When R$_1$ is a substituent other than hydrogen, it is particularly preferred that this R$_1$ group be in a meta or para position relative to the carbonyloxy group and in an ortho position relative to the R substituent. Further, in general, when R$_1$ is other than hydrogen, it is preferred that one of R or R$_1$ is located para to the carbonyloxy group and the other is located meta to the carbonyloxy group. Similarly, it is preferred that the R$_4$ substituent on the other phenyl ring is located para or meta, more preferably para, relative to the ether linking group.

The aromatic esters (e) will generally have a molecular weight in the range from about 700 to about 3,500, preferably from about 700 to about 2,500.

Fuel-soluble salt(s)s of the compounds (e) can be readily prepared for those compounds containing an amino or substituted amino group and such salt(s)s are contemplated to be useful for preventing or controlling engine deposits. Suitable salt(s)s include, for example, those obtained by protonating the amino moiety with a strong organic acid, such as an alkyl- or arylsulfonic acid. Preferred salt(s)s are derived from toluenesulfonic acid and methanesulfonic acid.

When the R or R$_1$ substituent is a hydroxy group, suitable salt(s)s can be obtained by deprotonation of the hydroxy group with a base. Such salt(s)s include salt(s)s of alkali metals, alkaline earth metals, ammonium and substituted ammonium salt(s)s. Preferred salt(s)s of hydroxy-substituted compounds include alkali metal, alkaline earth metal and substituted ammonium salt(s)s.

f) Quaternary Ammonium Salt

The quaternary ammonium salt additive is suitably the reaction product of a nitrogen-containing species having at least one tertiary amine group and a quaternising agent.

The nitrogen containing species may be selected from:

(x) the reaction product of a hydrocarbyl-substituted acylating agent and a compound comprising at least one tertiary amine group and a primary amine, secondary amine or alcohol group;

(y) a Mannich reaction product comprising a tertiary amine group; and (z) a polyalkylene substituted amine having at least one tertiary amine group.

Examples of quaternary ammonium salt and methods for preparing the same are described in the following patents, which are hereby incorporated by reference, US2008/0307698, US2008/0052985, US2008/0113890 and US2013/031827.

The preparation of some suitable quaternary ammonium salt additives in which the nitrogen-containing species includes component (x) is described in WO 2006/135881 and WO2011/095819.

Component (y) is a Mannich reaction product having a tertiary amine. The preparation of quaternary ammonium salts formed from nitrogen-containing species including component (y) is described in US 2008/0052985.

The preparation of quaternary ammonium salt additives in which the nitrogen-containing species includes component (z) is described for example in US 2008/0113890.

To form the quaternary ammonium salt additive (f) the nitrogen-containing species having a tertiary amine group is reacted with a quaternising agent.

The quaternising agent may suitably be selected from esters and non-esters.

Preferred quaternising agents for use herein include dimethyl oxalate, methyl 2-nitrobenzoate, methyl salicylate and styrene oxide or propylene oxide optionally in combination with an additional acid.

An especially preferred additional quaternary ammonium salt for use herein is formed by reacting methyl salicylate or dimethyl oxalate with the reaction product of a polyisobutylene-substituted succinic anhydride having a PIB number average molecular weight of 700 to 1300 and dimethylaminopropylamine.

Other suitable quaternary ammonium salts include quaternised terpolymers, for example as described in US2011/0258917; quaternised copolymers, for example as described in US2011/0315107; and the acid-free quaternised nitrogen compounds disclosed in US2012/0010112.

Further suitable quaternary ammonium compounds for use in the present invention include the quaternary ammonium compounds described in the applicants copending applications WO2011095819, WO2013/017889, WO2015/011506, WO2015/011507, WO2016/016641 and PCT/GB2016/052312.

The fuel compositions of the invention may contain, in addition to the quaternary ammonium salt additive(s) (i) and the gasoline, and the other components (ii) (selected from (a)-(f) described above) when present, unreacted raw materials and other reaction products and any of the other additives conventionally added to gasoline as, for example, other detergents, dispersants, anti-oxidants, anti-icing agents, metal deactivators, lubricity additives, friction modifiers, dehazers, corrosion inhibitors, dyes, markers, octane improvers, anti-valve-seat recession additives, stabilisers, demulsifiers, antifoams, odour masks, conductivity improvers, combustion improvers, etc.

Such further ingredients could in principle be added separately to quaternary ammonium compound(s) (i) but it is preferred for reasons of convenience and consistency of dosing to add them with quaternary ammonium compound(s) (i) and—when present, with further additive compounds (ii)—in a common additive composition.

Preferably the compound(s) (i) and (ii) (when present) is/are present in the fuel in the fuel storage tank which supplies the engine. Although they could be mixed into the fuel in the storage tank, preferably they are present in bulk fuel which is pumped into the storage tank.

The present invention relates to improving the performance of spark ignition engines by combusting gasoline fuel compositions comprising a quaternary ammonium salt additive.

The quaternary ammonium salt additives may be added to gasoline fuel at any convenient place in the supply chain. For example, the additives may be added to fuel at the refinery, at a distribution terminal or after the fuel has left the distribution terminal. If the additive is added to the fuel after it has left the distribution terminal, this is termed an aftermarket application. Aftermarket applications include such circumstances as adding the additive to the fuel in the delivery tanker, directly to a customer's bulk storage tank, or directly to the end user's vehicle tank. Aftermarket applications may include supplying the fuel additive in small bottles suitable for direct addition to fuel storage tanks or vehicle tanks.

The second aspect of the present invention provides a method of controlling deposits in spark ignition engine. Preferably the engine is a direct injection spark ignition gasoline engine.

Controlling deposits in the specification is intended to cover one or more of: reducing existing deposits ("clean-up"); reducing deposit formation ("keep-clean"); modifying deposits so as to reduce their negative effects.

It has surprisingly been found that the gasoline compositions used in this invention achieve good control of deposits in spark ignition gasoline engines.

It has surprisingly been found that the gasoline compositions used in this invention achieve good control of deposits even in the demanding context of the direct injection spark ignition gasoline engine.

This control of deposits may lead to a significant reduction in maintenance costs and/or an increase in power and/or an improvement in fuel economy.

Suitably the present invention provides a method of controlling deposits in a direct injection spark ignition gasoline engine, the method comprising the method comprising adding into the gasoline to be combusted:

(i) one or more quaternary ammonium salt additives of the first aspect and (ii) optionally, one or more additional components selected from a)-f) described above.

Suitably the present invention provides a method of improving the efficiency of a direct injection spark ignition gasoline engine, the method comprising adding into the gasoline to be combusted:

(i) one or more quaternary ammonium salt additives of the first aspect; and (ii) optionally, one or more additional components selected from a)-f) described above.

Suitably the present invention provides a method of operating a direct injection spark ignition gasoline engine, the method comprising adding into the gasoline to be combusted:

(i) one or more quaternary ammonium salt additives of the first aspect; and (ii) optionally, one or more additional components selected from a)-f) described above wherein the method provides one or more of:— improved fuel economy reduced maintenance less frequent overhaul or replacement of injectors improved driveability improved power improved acceleration Suitably the present invention provides the use of (i) one or more quaternary ammonium salt additives as defined in the first aspect and, optionally of (ii) one or more additional components selected from a)-f) described above; added into gasoline to control deposits in a direct injection spark ignition gasoline engine.

Suitably the present invention provides the use of (i) one or more quaternary ammonium salt additives as defined in the first aspect and, optionally of (ii) one or more additional components selected from a)-f) described above; added into gasoline to improve efficiency in a direct injection spark ignition gasoline engine.

Suitably the present invention provides the use of a gasoline comprising (i) one or more quaternary ammonium salt additives as defined in the first aspect and, optionally of (ii) one or more additional components selected from a)-f) described above; in a direct injection spark ignition gasoline engine to provide one or more of:— improved fuel economy reduced maintenance less frequent overhaul or replacement of injectors improved driveability improved power improved acceleration Any feature of the invention may be combined with any other feature as appropriate.

The invention will now be further described with reference to the following non-limiting examples. In the examples which follow the values given in parts per million (ppm) for treat rates denote active agent amount, not the amount of a formulation as added, and containing an active agent. All parts per million are by weight.

EXAMPLE 1

Additive A1, a quaternary ammonium salt additive of the invention was prepared as follows:

(a) A mixture of alkenes having 20 to 24 carbon atoms was heated with 1.2 molar equivalents of maleic anhydride. On completion of the reaction excess maleic anhydride was removed by distillation. The anhydride value of the substituted succinic anhydride product was measured as 2.591 mmolg$^{-1}$.

This product was then heated with one molar equivalent of polypropylene glycol having a number average molecular weight of 425, and the reaction was monitored by FTIR to provide the half ester/half acid product.

(b) 1 molar equivalent of diethyl ethanolamine was reacted with 1.5 molar equivalents of butylene oxide and 6 molar equivalents of water at 60° C. in toluene for 10 hours in the presence of the half ester/half acid provided in the step (a) to form a quaternary ammonium compound. Volatiles were removed in vacuo.

Compounds A2 to A21 detailed in table 1 were prepared by an analogous method.

TABLE 1

| Compound | R | H-(OR$^4$)n-OR$^5$ | Amine | Epoxide |
|---|---|---|---|---|
| A1 | C20-24 | polypropylene glycol Mn425 | Diethyl ethanolamine | Butylene oxide |
| A2 | C20-24 | polypropylene glycol Mn425 | Dimethyl ethanolamine | Butylene oxide |
| A3 | C20-24 | polypropylene glycol Mn425 | Triethylamine | Butylene oxide |
| A4 | C20-24 | polypropylene glycol Mn425 | Tributylamine | Butylene oxide |
| A5 | C20-24 | tripropylene glycol | Dimethyl ethanolamine | Butylene oxide |
| A6 | C20-24 | tripropylene glycol | Diethyl ethanolamine | Butylene oxide |
| A7 | C20-24 | tripropylene glycol | Triethylamine | Butylene oxide |
| A8 | C20-24 | tripropylene glycol | Tributylamine | Butylene oxide |
| A9 | C20-24 | triethyleneglycol | Dimethyl ethanolamine | Butylene oxide |
| A10 | C20-24 | triethyleneglycol | Diethyl ethanolamine | Butylene oxide |
| A11 | C20-24 | triethyleneglycol | Triethylamine | Butylene oxide |
| A12 | C20-24 | triethyleneglycol | Tributylamine | Butylene oxide |
| A13 | C20-24 | polypropylene glycol Mn725 | Dimethyl ethanolamine | Butylene oxide |
| A14 | C20-24 | polypropylene glycol Mn725 | Diethyl ethanolamine | Butylene oxide |
| A15 | C20-24 | polypropylene glycol Mn725 | Triethylamine | Butylene oxide |
| A16 | C20-24 | polypropylene glycol Mn725 | Tributylamine | Butylene oxide |
| A17 | C20-24 | Tetraethyleneglycol | Dimethyl ethanolamine | Butylene oxide |
| A18 | C20-24 | Tetraethyleneglycol | Diethyl ethanolamine | Butylene oxide |
| A19 | C20-24 | tetraethyleneglycol | Triethylamine | Butylene oxide |
| A20 | C20-24 | tetraethyleneglycol | Tributylamine | Butylene oxide |
| A21 | C20-24 | polyethyleneglycol Mn400 | Dimethyl ethanolamine | Butylene oxide |
| A22 | C20-24 | 2-Ethylhexanol | N,N-diethyl ethanolamine | Butylene oxide |
| A23 | C20-24 | Butanol | N,N-diethyl ethanolamine | Butylene oxide |
| A24 | C20-24 | Poly(ethylene glycol) Mn400 | 2-[2-(Dimethylamino)ethoxy] ethanol | 1,2-epoxydodecane |
| A25 | C20-24 | Poly(ethylene glycol) Mn400 | N,N-dimethyl Benzylamine | 2-Ethylhexyl Glycidyl Ether |
| A26 | C20-24 | Poly(ethylene glycol) Mn400 | N,N-dimethyl ethanolamine | 1,2-epoxydodecane |
| A27 | C20-24 | Poly(ethylene glycol) Mn400 | N,N-dimethyl ethanolamine | Styrene Oxide |
| A28 | C20-24 | Poly(ethylene glycol) Mn400 | N,N-Dimethyl octadecylamine | 2-Ethylhexyl Glycidyl Ether |
| A29 | C20-24 | Poly(ethylene glycol) Mn400 | N,N-Dimethyl octadecylamine | Butylene oxide |
| A30 | C20-24 | Poly(ethylene glycol) Mn400 | N,N-Dimethyl octadecylamine | 1,2-epoxydodecane |
| A31 | C20-24 | Poly(ethylene glycol) Mn400 | N,N-Dimethyl octadecylamine | Styrene Oxide |
| A32 | C20-24 | Poly(propylene glycol) Mn425 | N,N-dimethyl Benzylamine | 2-Ethylhexyl Glycidyl Ether |
| A33 | C20-24 | Poly(propylene glycol) Mn425 | N,N-dimethyl Benzylamine | Butylene oxide |
| A34 | C20-24 | Poly(propylene glycol) Mn425 | N,N-dimethyl Benzylamine | Styrene Oxide |
| A35 | C20-24 | Poly(propylene glycol) Mn425 | N,N-dimethyl Benzylamine | 1,2-epoxydodecane |
| A36 | C20-24 | Poly(propylene glycol) Mn425 | N,N-Dimethyl octadecylamine | 2-Ethylhexyl Glycidyl Ether |
| A37 | C20-24 | Poly(propylene glycol) Mn425 | N,N-Dimethyl octadecylamine | Butylene oxide |
| A38 | C20-24 | Poly(propylene glycol) Mn425 | N,N-Dimethyl octadecylamine | Styrene Oxide |

TABLE 1-continued

| Compound | R | H-(OR⁴)n-OR⁵ | Amine | Epoxide |
|---|---|---|---|---|
| A39 | C20-24 | Tetradecanol | N,N-diethyl ethanolamine | Butylene oxide |
| A40 | C20-24 | Tri(propylene glycol) | 2-[2-(Dimethylamino)ethoxy] ethanol | 2-Ethylhexyl Glycidyl Ether |
| A41 | C20-24 | Tri(propylene glycol) | 2-[2-(Dimethylamino)ethoxy] ethanol | 1,2-epoxydodecane |
| A42 | C20-24 | Tri(propylene glycol) | 2-[2-(Dimethylamino)ethoxy] ethanol | Styrene Oxide |
| A43 | C20-24 | Tri(propylene glycol) | N,N-dimethyl Benzylamine | 2-Ethylhexyl Glycidyl Ether |
| A44 | C20-24 | Tri(propylene glycol) | N,N-dimethyl Benzylamine | Butylene oxide |
| A45 | C20-24 | Tri(propylene glycol) | N,N-dimethyl Benzylamine | 1,2-epoxydodecane |
| A46 | C20-24 | Tri(propylene glycol) | N,N-dimethyl Benzylamine | Styrene Oxide |
| A47 | C20-24 | Tri(propylene glycol) | N,N-dimethyl ethanolamine | 1,2-epoxydodecane |
| A48 | C20-24 | Tri(propylene glycol) | N,N-Dimethyl octadecylamine | 2-Ethylhexyl Glycidyl Ether |
| A49 | C20-24 | Tri(propylene glycol) | N,N-Dimethyl octadecylamine | Butylene oxide |
| A50 | C20-24 | Tri(propylene glycol) | N,N-Dimethyl octadecylamine | 1,2-epoxydodecane |
| A51 | C20-24 | Tri(propylene glycol) | N,N-Dimethyl octadecylamine | Styrene Oxide |
| A52 | 1000PIB | Tri(propylene glycol) | N,N-dimethyl ethanolamine | 1,2-epoxydodecane |

The invention claimed is:

1. A quaternary ammonium compound of formula (I):

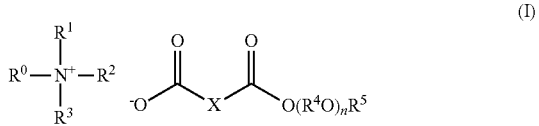

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

2. A method of preparing a quaternary ammonium salt, the method comprising reacting (a) a tertiary amine of formula $R^1R^2R^3N$ with (b) an acid-derived alkylating agent in the presence of (c) a compound of formula HOOCXCOO—$(R^4O)_n$—$R^5$, wherein $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

3. The method according to claim 2 wherein component (b) is an epoxide.

4. A composition comprising a quaternary ammonium compound of formula (I):

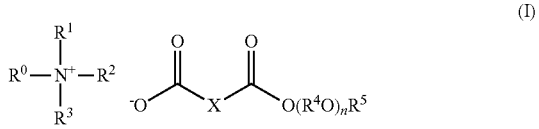

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

5. The composition according to claim 4 wherein the composition is an additive composition for a fuel or lubricating oil.

6. The composition according to claim 4 wherein the composition is a fuel composition.

7. A method of improving the performance of an engine, the method comprising combusting in the engine a fuel composition comprising as an additive a quaternary ammonium compound of formula (I):

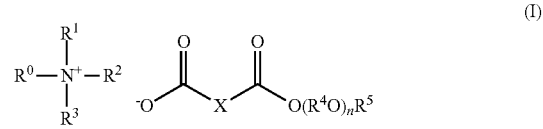

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

8. The salt according to claim 1 wherein HOOCXCOO—$(R^4O)_n$—$R^5$ is derived from a hydrocarbyl substituted succinic acid or a hydrocarbyl substituted succinic anhydride.

9. The salt according to claim 1 wherein each $R^4$ is ethylene or propylene.

10. The salt according to claim 1 wherein $R^5$ is hydrogen and n is at least 1.

11. The salt according to claim 1 wherein $R^5$ is an optionally substituted alkyl group having 4 to 40 carbon atoms and n is from 0 to 40.

12. The salt according to claim 1 wherein each of $R^1$ and $R^2$ is independently an optionally substituted alkyl group having from 1 to 12 carbon atoms.

13. The salt according to claim 1 wherein $R^3$ is an alkyl or hydroxyalkyl group having 1 to 10 carbon atoms.

14. The salt according to claim 1 wherein $R^3$ is selected from the group consisting of:
(1) a polyisobutenyl group having a molecular weight of from 100 to 5000;
(2) an optionally substituted alkylene phenol moiety of formula (A) or (B)

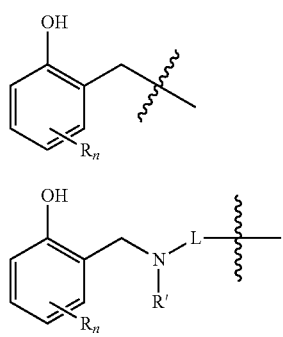

wherein n is 0 to 4, R is an optionally substituted hydrocarbyl group, R' is an optionally substituted alkyl, alkenyl or aryl group; and L is a linking group; and
(3) a succinimide moiety of formula:

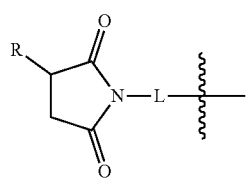

wherein R is an optionally substituted hydrocarbyl group and L is a linking group.

15. The salt according to claim 1 wherein $R^0$ as is a group of formula:

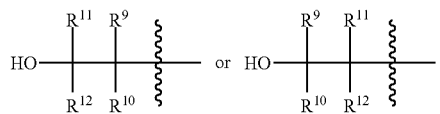

wherein each of $R^9$, $R^{10}$, $R^{11}$, $R^{12}$ is independently hydrogen or an optionally substituted alkyl, alkenyl or aryl group.

16. The salt according to claim 1 wherein X is an optionally substituted alkylene or arylene group.

17. The salt according to claim 1 wherein the quaternary ammonium compound is the reaction product of:
(a) a tertiary amine of formula $R^1R^2R^3N$ wherein each of, $R^1$, $R^2$ and $R^3$ is independently an optionally substituted alkyl group having 1 to 12 carbon atoms;
(b) an epoxide selected from the group consisting of: styrene oxide, ethylene oxide, propylene oxide, butylene oxide, epoxyhexane, octene oxide, stilbene oxide, 2-ethylhexyl glycidyl ether, 1,2-epoxydodecane and other alkyl and alkenyl epoxides having 2 to 50 carbon atoms; and
(c) a compound of formula $HOOCXCOO-(R^4O)_n-R^5$ wherein X is $CH_2CHR$ or $CHRCH_2$ wherein R is an optionally substituted hydrocarbyl group; and n is more than 1, $R^4$ is an ethylene or propylene group and $R^5$ is hydrogen; or
n is 0 or and $R^5$ is a C1 to C20 alkyl group.

18. The salt according to claim 1 wherein the quaternary ammonium compound is the reaction product of:
(a) a tertiary amine of formula $R^1R^2R^3N$ wherein each of, $R^1$, $R^2$ and $R^3$ is independently an alkyl or hydroxyalkyl group having 1 to 6 carbon atoms;
(b) an epoxide selected from the group consisting of: propylene oxide, butylene oxide and 2-ethylhexyl glycidyl ether; and
(c) a compound of formula $HOOCXCOO-(R^4O)_n-R^5$ which is the reaction product of a succinic acid or anhydride having a $C_{20}$ to $C_{24}$ alkyl or alkenyl substituent and an alcohol selected from the group consisting of: polypropylene glycol having a number average molecular weight of 300 to 800, 2-ethylhexanol and butanol.

19. The composition according to claim 4 wherein the composition is a lubricating composition.

20. The composition according to claim 4 wherein the composition is a gasoline fuel composition.

21. The composition according to claim 20 wherein the gasoline fuel composition comprises one or more further additives selected from the group consisting of:
a) carrier oils;
b) acylated nitrogen compounds which are the reaction product of a carboxylic acid-derived acylating agent and an amine;
c) hydrocarbyl-substituted amines wherein the hydrocarbyl substituent is substantially aliphatic and contains at least 8 carbon atoms;
d) mannich base additives comprising nitrogen-containing condensates of a phenol, aldehyde and primary or secondary amine;
e) aromatic esters of a polyalkylphenoxyalkanol; and
f) additional quaternary ammonium salts.

22. The composition according to claim 20 wherein the gasoline fuel composition comprises a mixture of two or more quarternary ammonium salt additives.

23. The method as defined in claim 7 wherein the additive is used as a detergent to combat deposits in a gasoline fuel composition in a spark ignition engine.

24. The method according to claim 7 wherein the engine is a direct injection spark ignition engine.

25. The method according to claim 7 which achieves "keep clean" performance.

26. The method according to claim 7 which achieves "clean up" performance.

27. The method according to claim 7 wherein the deposits are injector deposits.

28. The method according to claim 27 wherein the deposits are internal injector deposits.

29. The method according to claim 7 which combats intake valve deposits.

30. The method according to claim 7 which achieves an improvement in performance of one or more of:
improved fuel economy;
reduced maintenance;
less frequent overhaul or replacement of injectors;
improved driveability;
improved power; or
improved acceleration.

* * * * *

UNITED STATES PATENT AND TRADEMARK OFFICE
CERTIFICATE OF CORRECTION

Page 1 of 1

PATENT NO. : 11,186,791 B2
APPLICATION NO. : 16/496162
DATED : November 30, 2021
INVENTOR(S) : Alan Norman Ross et al.

It is certified that error appears in the above-identified patent and that said Letters Patent is hereby corrected as shown below:

In the Claims

In Column 41 of Claim 1, Line 46:
"acid-derived"
Should read:
-- acid-activated --

Signed and Sealed this
First Day of March, 2022

Drew Hirshfeld
*Performing the Functions and Duties of the*
*Under Secretary of Commerce for Intellectual Property and*
*Director of the United States Patent and Trademark Office*